United States Patent
Marcuccio et al.

(10) Patent No.: US 6,713,566 B1
(45) Date of Patent: Mar. 30, 2004

(54) ORGANOBORON DERIVATIVES AND PROCESS FOR COUPLING ORGANIC COMPOUNDS

(75) Inventors: Sebastian Mario Marcuccio, Endeavour Hills (AU); Mary Rodopoulos, Blackburn South (AU); Helmut Weigold, Mount Waverley (AU); Peter Osvath, South Yarra (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/821,464

(22) PCT Filed: Oct. 14, 1999

(86) PCT No.: PCT/AU99/00882
§ 371 (c)(1),
(2), (4) Date: Aug. 6, 2001

(87) PCT Pub. No.: WO00/21966
PCT Pub. Date: Apr. 20, 2000

(30) Foreign Application Priority Data

Oct. 14, 1998 (AU) .......................................... PP6494/98

(51) Int. Cl.$^7$ .............................. C08F 8/00; C07F 5/02; C07F 5/04
(52) U.S. Cl. .............................. 525/337; 568/1; 568/6; 564/8; 585/525
(58) Field of Search .............................. 525/337; 568/1; 568/6; 564/8; 585/525

(56) References Cited

FOREIGN PATENT DOCUMENTS

| WO | WO 99/12940 A | 3/1999 |
| WO | WO 99/33845 A | 7/1999 |
| WO | WO 98/58935 A | 12/1999 |

OTHER PUBLICATIONS

Ishiyama T et al., Diboration of alkenes with bis(pinacolato)diboron catalysed by platinum(0) complex, Chem Commun (1997) 7 689–690.
Lawson YG et al., Platinum catalysed 1,4–diboration of α,β–unsaturated ketones, Chem Commun (1997) 21, 2051–2052.
Ishiyama T et al., A synthesis of (E)–(1–organo–1–alkenyl)boronates by the palladium–catalysed cross–coupling reaction of (E)–1, 2–bis(boryl)–1–alkenes wih organic halides: a formal carboboration of alkenes via the diboration coupling sequence, Chem Letters (1996) 12, 1117–1118.
Chemical Abstract 120:8636 & Ishiyama T et al., Platinum(0)–catalysed diboration of alkynes, J Am Chem Soc (1993) 115(23), 11018–19.
Chemical Abstract 125:301049 & Ishiyama T et al., A synthesis of allyboronates via the palladium(0)–catalysed cross–coupling reaction of bis(pinacolato)diboron with allylic acetates, Tetrahedron Lett (1996) 37(38), 6889–6892.
Chemical Abstract 127:50682 & Suzuki A, Haloboration of alkynes and related reactions, Spec Pipl—R Soc Chem, (1997) 2201 (Advances in Boron Chemistry) 163–170.
Chemical Abstract 127:277979 & Ahiko T et al., A sequence of palladium catalysed borylation of allyl acetates with bis(pinacolato)diboron and intramolecular allylboration for the cyclization of oxo–2–alkenyl acetates, Chem Letters (1997) 8, 811–812.
Chemical Abstract 131:130018, Ishiyama T et al., Synthesis of organoboron compounds via the transition metal–catalyzed addition reaction of (alkoxo)diborons.
Ishiyama, T. et al., "Platinum(0)–Catalyzed Diboration of Alkynes with Tetrakis(alkoxo)diborons", Organometallics, vol. 15, 1996, pp. 713–720, XP002185106.
Ishiyama, T. et al., "Platinum(0)–catalysed diboration of alka–1, 3–dienes with bis(pinacolato)diboron", Chem. Commun., 1996, pp. 2073–2074, XP002185107.
Ishiyama, T. et al., "Synthesis of Arylboronates via the Palladium(0)–Catalyzed Cross–Coupling Reaction of Tetra(alkoxo)diborons with Aryl Triflates", Tetrahedron Letters, vol. 38, No. 19, 1997, pp. 3447–3450, XP000686267.
Ishiyama, T. et al., "Platinum(0)–Catalyzed Diboration of Allenes with Bis(pinacolato)=diboron", Tetrahedron Letters, vol. 39, 1998, pp. 2357–2360, XP004111172.

*Primary Examiner*—Jeffrey Mullis
(74) *Attorney, Agent, or Firm*—Bacon & Thomas

(57) ABSTRACT

This invention relates to a process for covalently coupling organic compounds which comprises: reacting an olefinic compound having at least one carbon to carbon double bond or an acetylenic compound having at least one carbon to carbon triple bond with a diboron derivative in the presence of a Group 8–11 metal catalyst to form an organoboron intermediate having an organoboronate residue on at least one carbon atom of the respective double or triple bond; and reacting the organoboron intermediate with an organic compound having a halogen or halogen-like substituent at a coupling position in the presence of a Group 8–11 metal catalyst and a suitable base, whereby the olefinic or acetylenic compound is coupled to the organic compound via a direct bond between the carbon atom having the organoboronate residue and the coupling posiitijno. This invention also relates to a process for preparing an organoboron derivative which comprises reacting an olefinic compound having a leaving group in at the allylic position with a diboron derivative in the presence of a Group 8–11 metal catalyst such that the leaving gruop is replaced with an organoboronate residue. The invention further relates to organoborn intermediates and their preparation.

41 Claims, No Drawings

ORGANOBORON DERIVATIVES AND PROCESS FOR COUPLING ORGANIC COMPOUNDS

The present invention relates to a process for covalently coupling organic compounds, in particular to a process for covalently linking an olefinic or acetylenic compound via an organoboron intermediate to other organic compounds. The invention also relates to a process for preparing the organoboron intermediates.

Processes for forming covalent bonds between olefinic or acetylenic compounds and other organic compounds, both inter- and intra-molecular, are of particular importance to the synthetic organic chemist. Many such reactions are known, each requiring its own special reaction conditions, solvents, catalysts, activating groups etc. Some known types of coupling reactions involving olefinic moieties include the Michael reaction and reactions described in the following references: Transition Metals in the Synthesis of Complex Organic Molecules (L. S. Hegedus, University Science Books, 1994, ISBN 0-935702-28-8); Handbook of Palladium Catalysed Organic Reactions (J. Malleron, J. Fiaud and J. Legros, Academic Press, 1997, ISBN 0-12-466615-9); Palladium Reagents and Catalysts (Innovations in Organic Synthesis by J. Tsuji, John Wiley & Sons, 1995, ISBN 0471-95483-7); and N. Miyuara and A. Suzuki, Chem Rev. 1995, 95, 2457-2483.

Catalysts of palladium, its complexes and its salts are well recognised for activation of C—H bonds towards coupling reactions. In this regard the Heck reaction of an alkene or alkyne with an aryl or vinyl halide in the presence of palladium derivatives has been the subject of intensive study. However commercial development of the Heck reaction has not progressed as rapidly as could have been expected. Other Group 8–11 metal catalysts, such as platinum, have also been used to activate such carbon bonds.

The success of the Heck reaction depends to a large extent on the substrates and the reaction conditions. For example, when two β-hydrogens are present in the alkene the reaction generally leads to the formation of the (E)-alkenes which are often contaminated with the corresponding (Z)-alkenes.

Although alkene borates (alkenylborates) can be reacted with a variety of organic molecules to give coupled products via the formation of new carbon-carbon bonds (See for example the references above) the process for the preparation of the alkenylborates by the commonly used hydroboration reaction of alkynes is limited because of the difficulties that are encountered through the lack of regiochemistry and/or chemoselectivity (such as the reduction of a number of different functional groups) (See N. Miyuara and A. Suzuki, Chem Rev. 1995, 95, 2457–2483).

Improved and/or alternative methodologies are thus required for the synthesis of organo borates from alkenes and alkynes.

It has now been found that useful organoboron compounds can be synthesised from alkenes and alkynes under mild conditions and in the presence of a range of substituents. This process overcomes or at least alleviates one or more of the limitations encountered in the use of the standard hydroboration methodology. Coupling of the organoboron derivatives with an organic compound may be achieved in the presence of Group 8–11 metal catalyst and a suitable base.

Accordingly the present invention provides a process for covalently coupling organic compounds which comprises reacting an olefinic organic compound having at least one carbon to carbon double bond or an acetylenic compound having at least one carbon to carbon triple bond with a diboron derivative in the presence of a Group 8–11 metal catalyst such that an organoboronate residue is introduced on one or two of the carbon atoms of the respective double or triple bond. In this process the triple bond becomes a double bond, or the double bond becomes a single bond. Other triple or double bonds may be present and, depending on the reaction conditions employed, these may or may not also react with the diboron derivative.

The diboron derivative may be an ester or other stable derivative of diboronic acid. Examples of suitable esters include those of the formula $(RO)_2B—B(OR)_2$ where R is optionally substituted alkyl or optionally substituted aryl or $—B(OR)_2$ represents a cyclic group of formula

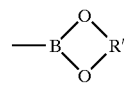

where R' is optionally substituted alkylene, arylene or other divalent group comprising linked aliphatic or aromatic moieties. Preferred diboron derivatives include 4,4,4',4',5,5,5', 5'-octamethyl-2,2'-bi-1,3,2-dioxaborolane[bis(pinacolato) diboron or the pinacol ester of diboronic acid], 2,2'-bi-1,3, 2-dioxaborolane[bis(ethanediolato)diboron], 2,2'-bi-1,3,2-dioxaborinane[bis(n-propanediolato)diboron], 5,5,5',5'-tetramethyl-2,2'-bi-1,3,2-dioxaborinane[bis (neopentanediolato)diboron], (4R,4'R,5R,5'R)-tetramethyl-2,2'-bi-1,3,2-dioxaborolane, 1,1,2,2-tetrakis(2-methoxyethyloxy)diborane, bis((1S,2S,3R,5S)-(+)-pinanediolato)diboron(B—B), (4R,4'R)-diphenyl-2,2'-bi-1, 3,2-dioxaborolane, (+/−)-4,4'-bi-[(4-methoxyphenoxy) methyl]-2,2'-bi-1,3,2-dioxaborolane, 2,2'-bi-(3aR,7aS) hexahydro-1,3,2-benzodioxaborole, tetraisopropyl (4R,4'R, 5R,5'R)-2,2'-bi-1,3,2-dioxaborolane-4,4'5,5'-tetracarboxylate, (3aR,3'aR,6aS,6'aS)-di-tetrahydro-3aH-cyclopenta[d]-2,2'-bi-1,3,2-dioxaborolane, (3R,6S,3'R,6'S)-di-tetrahydrofuro[3,4-d]-2,2'-bi-1,3,2-dioxaborolane, (+/−)-4,4'-bi-(methoxymethyl)-2,2'-bi-1,3,2-dioxaborolane, 2,2'-bi-1,3,2-dioxaborepane, 5,5'-dihydroxymethyl-5,5'-dimethyl-2,2'-bi-1,3,2-dioxaborinane, bis(1R,2R,3S,5R-(−)-pinanediolato)diboron(B—B), 2,2'-bi-4H-1,3,2-benzodioxaborinine, (+/−)4,4'-bi-(phenoxymethyl)-2,2'-1,3, 2-dioxaborolane, (+/−)4,4,4',4 ',6,6'-hexamethyl-2,2'-bi-1,3, 2-dioxaborinane, 5,5,5',5'-tetraethyl-2,2'-bi-1,3,2-dioxaborinane, 4,4',5,5'-tetramethyl-2,2'-bi-1,3,2-dioxaborolane, (+/−)-4,4'-dimethyl-2,2'-bi-1,3,2-dioxaborinane, (+/−)-5,5'-dimethyl-2,2'-bi-1,3,2-dioxaborinane, bi-(dinaphtho[2,1-d: 1,2-f])-2,2'-bi-1,3,2-dioxaborepine, 6,6'-diethyl-2,2'-bi-1,3,6,2-dioxazaborocane, 6,6'-dimethyl-2,2'-bi-1,3,6,2-dioxazaborocane, 5,5,5',5'-tetraphenyl-2,2'-bi-1,3,2-dioxaborinane, 4,4,4',4',7,7,7',7'-octamethyl-2,2'-bi-1,3, 2dioxaborepane, 1,1,2,2-tetrakis(neopentyloxy)diborane, (4S,4'S,5S,5'S)-tetramethyl-2,2'-bi-1,3,2-dioxaborolane, tetrabutyl (4R,4'R,5R,5'R)-2,2'-bi-1,3,2-dioxaborolane-4,4',5, 5'-tetracarboxylate, (4R,4'R,5R,5'R)-N4,N4,N4',N4',N5,N5, N5',N5'-octamethyl-2,2'-bi-1,3,2-dioxaborolan e-4,4',5,5'-tetracarboxamide, 4,4,4',4'-tetramethyl-2,2'-bi-1,3,2-dioxaborinane. 4,4,4',4 ',6,6,6',6'-octamethyl-2,2'-bi-1,3,2-dioxaborinane, .3,3'-bi-1,5-dihydro-2,4,3-benzodioxaborepine, (+/−)4,4,4',4',5,5'-hexamethyl-2,2'-bi-1,3,2-dioxaborolane, 4,4,4',4'-tetramethyl-2,2'-bi-1,3, 2dioxaborolane, 5,5,5',5'-tetramethyl-2,2'-bi-1,3,2-dioxaborinane, 4,4',5,5'-tetraphenyl-1,3,2-dioxaborolane, 4,4'-diphenyl-1,3,2-dioxaborolane and 4,4',6,6'-tetra(tert-butyl)-1,3,2-benxodioxaborole.

Some of the diboron derivatives will be more readily amenable to subsequent hydrolysis than others and may allow for the use of milder reaction conditions. Furthermore, judicious choice of the diboron derivative used may facilitate control over the reaction products formed. The diboron ester derivatives may be made following the method of Brotherton et al. [R. J. Brotherton, A. L. McCloskey, L. L. Peterson and H. Steinberg, J. Amer. Chem. Soc. 82, 6242 (196); R. J. Brotherton, A. L. McCloskey, J. L. Boone and H. M. Manasevit,. J. Amer. Chem. Soc. 82, 6245 (1960)]. In this process $B(NMe_2)_3$, obtained by reaction of $BCl_3$ with $NHMe_2$, is converted to $BrB(NMe_2)_2$ by reaction with a stoichiometric amount of $BBr_3$. Reduction in refluxing toluene with sodium metal gives the diboron compound $[B(NMe_2)_2]_2$ which, after purification by distillation, can be reacted with the alcohol (for example, pinacol) in the presence of a stoichiometric amount of HCl to give the desired ester product. Bis(neopentanediolato)diboron is described by Nguyen et al [Nguyen, P., Lesley, G., Taylor, N. J., Marder, T. B., Pickett, N/L/, Clegg, W., Elsegood, M. R. J., and Norman, N. C., *Inorganic Chem.* 1994, 33, 4623–24]. Other methods for the preparation of the diboron derivatives would be known to those in the art.

The term "organoboronate residue" as used herein refers to the single boron containing residue formed by cleavage of the boron to boron bond of a diboron derivative. Examples of organoboronate residues are groups of the formula —$B(OR)_2$ as defined above.

The terms "organoboron derivative" and "organoboron intermediate" as used herein refer to an organic compound having at least one organoboronate residue at a substitution position.

According to another embodiment of the invention there is provided a process for covalently coupling organic compounds which comprises:
  reacting an olefinic compound having at least one carbon to carbon double bond or an acetylenic compound having at least one carbon to carbon triple bond with a diboron derivative in the presence of a Group 8–11 metal catalyst to form an organoboron intermediate having an organoboronate residue on at least one carbon atom of the respective double or triple bond, and
  reacting the organoboron intermediate with an organic compound having a halogen or halogen-like substituent at a coupling position in the presence of a Group 8–11 metal catalyst and a suitable base, whereby the olefinic or acetylenic compound is coupled to the organic compound via a direct bond between the carbon atom having the organoboronate residue and the coupling position.

It is to be appreciated that the olefinic or acetylenic compound and the organic compound may be one and the same compound such that the coupling reaction is intramolecular.

It is especially convenient to conduct the process in a single pot without isolation of the organoboron intermediate, however it has been found that the presence of unreacted diboron derivative can interfere with the coupling step, resulting in the formation of unwanted by-products.

Accordingly in another embodiment of the present invention there is provided a process for covalently coupling organic compounds which comprises:
  reacting an olefinic compound having at least one carbon to carbon double bond or an acetylenic compound having at least one carbon to carbon triple bond with a diboron derivative in the presence of a Group 8–11 metal catalyst to form an organoboron intermediate having an organoboronate residue on at least one carbon atom of the respective double or triple bond,
  adding water or water and a suitable base to decompose excess diboron derivative, and
  reacting the organoboron intermediate with an organic compound having a halogen or halogen-like substituent at a coupling position in the presence of a Group 8–11 metal catalyst and a suitable base, whereby the olefinic or acetylenic compound is coupled to the organic compound via a direct bond between the carbon atom having the organoboronate residue and the coupling position.

Preferably the reaction is conducted in a single pot, although it is possible to isolate the organoboron intermediate prior to the final coupling step. If the reaction is conducted in a single pot it is preferred that the base added to decompose the diboron derivative is suitable for catalysing the coupling reaction. In this case there is no need to add stronger base with the organic compound in the coupling reaction.

In another embodiment, after formation of the organoboron intermediate, the coupling of the organoboron intermediate with the organic compound is achieved by increasing the temperature of the reaction mixture to a temperature sufficient for said coupling reacting to occur. In this embodiment it may not be necessary to add a stronger base to catalyse the coupling reaction.

In cases where there is a need to remove excess diboron derivative but the use of water or water and base is deleterious because of the sensitivity of substituents or other factors the excess diboron derivative may be decomposed by addition of mild oxidising agents following the formation of the organoboron intermediate.

Accordingly in a further embodiment there is provided a process for covalently coupling organic compounds which comprises:
  reacting an olefinic compound having at least one carbon to carbon double bond or an acetylenic compound having at least one carbon to carbon triple bond with a diboron derivative in the presence of a Group 8–11 metal catalyst to form an organoboron intermediate having an organoboronate residue on at least one carbon atom of the respective double or triple bond,
  adding a mild oxidising agent to decompose excess diboron derivative, and
  reacting the organoboron intermediate with an organic compound having a halogen or halogen-like substituent at a coupling position in the presence of a Group 8–11 metal catalyst and a suitable base, whereby the olefinic or acetylenic compound is coupled to the organic compound via a direct bond between the carbon atom having the organoboronate residue and the coupling position.

The mild oxidising agent may be any compound which will break the B—B bond of the diboron derivative but which is not strong enough to break boron-carbon bonds of the organoboron intermediate. Suitable mild oxidising agents are N-chlorosuccinimide, dioxygen gas, chloramine-T, chloramine-B, 1-chlorotriazole, 1,3-dichloro-5,5-dimethylhydantoin, trichloroisocyanuric acid and dichloroisocyanuric acid potassium salt.

Oxidants such as hydrogen peroxide, ozone, bromine, t-butyl hydroperoxide, potassium persulphate, sodium hypochlorite and peracids, are too strong for use in this process; use of strong oxidants does not form part of this invention.

The terms "olefinic" and "olefinic compound" as used herein refer to any organic compound having at least one carbon to carbon double bond which is not part of an aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,diene, cyclohexa-1,3-diene, cyclohexa-1,4-diene, cyclohepta-1,3,5-triene and cycloocta-1,3,5,7-tetraene, each of which may be optionally substituted. Preferably the straight chain branched or cyclic alkene contains between 2 and 20 carbon atoms.

The olefinic compounds may be $\alpha,\beta$-unsaturated carbonyl compounds such as $\alpha,\beta$-unsaturated esters, aldehydes, ketones, nitriles, or conjugated dienes such as 1,3-cyclopentadiene. The term "conjugated dienes" as used herein refers to any compound capable of acting as a diene in a Diels-Alder reaction. The olefinic compound may also be an organic compound having a leaving group in an allylic position or a compound having adjacent double bonds, such as a 1,2-diene.

The term "acetylenic compound" as used herein refers to any compound having at least one carbon to carbon triple bond. The acetylenic compounds may be selected from optionally substituted straight chain, branched or cyclic alkynes and molecules, monomers and macromolecules such as polymers and dendrimers, which include at least one carbon to carbon triple bond. Examples of suitable acetylene compounds include, but are not limited to acetylene, propyne, but-1-yne, but-2-yne, pent-1-yne, pent-2-yne, hex-1-yne, hex-2-yne, hex-3-yne, cyclohexyne, hep-1-yne, hept-2-yne, hept-3-yne, cycloheptyne, oct-1-yne, oct-2-yne, oct-3-yne, oct-4-yne, cyclooctyne, nonyne, decyne, 1,3,5-trioctyne, 2,4-dihexyne, each of which may be optionally substituted. Preferably the straight chain, branched or cyclic alkyne contains between 1 and 20 carbon atoms.

The olefinic or acetylenic compounds may have two or more double or triple bonds, or may have a combination of double and triple bonds. By selecting appropriate conditions it is possible to obtain organoboron derivatives in which one or more of these bonds remains intact. For example, where the compound has a double bond and a triple bond selection of a suitable catalyst can result in a product in which only the triple bond has reacted with the diboron derivative. Selection of another set of conditions and/or catalyst may result in preferential reaction at the double bond. Similarly the molar ratio of diboron compound to unsaturated compound may be selected to give a particular desired product. As mentioned above the presence of base can also affect the outcome of the reaction. It has also been found that heating the reaction mixture after initial reaction can result in some hydrodeboration, thereby altering the product, or proportion of different products, obtained from the reaction. For example it is possible to convert some or all of the diboronated product to the corresponding monoboronated product.

As used herein the term "organic compound having a halogen or halogen-like substituent at a coupling position" refers to any organic compound having a carbon to halogen or carbon to halogen-like substituent bond at a position where coupling to the organoboron compound is desired. The organic compound may be aliphatic, olefinic, allylic, acetylenic, aromatic, polymeric or dendritic. The compound may be an olefinic or acetylenic compound as defined above or part of such a compound. The organic compound may have one or more, preferably between 1 and 6, halogen or halogen-like substituents at coupling positions.

The terms "aromatic" and "aromatic compound(s)" as used herein refer to any compound or moiety which includes or consists of one or more aromatic or pseudoaromatic rings. The rings may be carbocyclic or heterocyclic, and may be mono or polycyclic ring systems. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The terms "aromatic" and "aromatic compound (s)" include molecules, and macromolecules, such as polymers, copolymers and dendrimers which include or consist of one or more aromatic or pseudoaromatic rings. The term "pseudoaromatic" refers to a ring system which is not strictly aromatic, but which is stablized by means of delocalization of $\pi$ electrons and behaves in a similar manner to aromatic rings. Examples of pseudoaromatic rings include but are not limited to furan, thiophene, pyrrole and the like.

The term "coupling position" as used herein refers to a position on an organic compound at which coupling to another organic compound is desired. Each olefinic compound or organic compound may have one or more, preferably between 1 and 6, coupling positions.

The term "substitution position" as used herein refers to a position on an organic compound at which substitution with an organoboronate residue is desired. Each organic compound may have one or more, preferably between 1 and 6, substitution positions. If the organic compound is a polymer or a dendrimer it may have many substitution positions.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxy silyl and arylphenoxy silyl. The optional substituent should not be significantly deleterious to the reactivity of the compound to which it is attached.

The organic compound with which the organoboron intermediate reacts must include at least one halogen or halogen-like substituent at a coupling position to enable reaction with the organoboron intermediate. Preferred halogen substituents include I, Br and Cl. The reactivity of chloro substituted aromatic ring compounds can be increased by selection of appropriate ligands on the Group 8–11 metal catalyst. The terms "halogen-like substituent" and "pseudo-halide" refer to any substituent which, if present on an organic compound may undergo substitution with an organoboron intermediate to give a coupled product. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0471-95483-7).

The present invention is based on the finding that in the presence of a Group 8–11 metal catalyst, diboron derivatives may add across a carbon to carbon double or triple bond of an olefinic or acetylenic compound such that an organoboronate residue is introduced on each of the carbon atoms of the respective double or triple bond, such that the double bond becomes a single bond and the triple bond becomes a double bond. In the case of two or more conjugated double bonds the organoboronate residues may be introduced on the distal carbon atoms participating in the conjugation resulting in loss of conjugation. In the case of an α,β-unsaturated carbonyl compound, the end-diboronate formed is unstable and the product isolated has a single organoboronate residue on the β-carbon and the α,β-unsaturation is lost.

The term "distal" as used herein in relation to carbon atoms participating in conjugation refers to the carbon atoms at each end of the conjugated chain of carbon atoms. For example, the distal carbon atoms in 1,3-butadiene are carbon atoms 1 and 4.

The expression "loss of conjugation" as used herein refers to the conversion of a double bond of a conjugated system into a single bond. This may result in complete loss of conjugation or partial loss of conjugation. In some cases there may be some rearrangement following loss of conjugation.

The process according to the present invention is especially suitable for coupling olefinic or acetylenic compounds containing substituents which are reactive with organometallic compounds, such as Grignard reagents or alkyl lithiums, and therefore unsuitable for reacting using standard Grignard methodology unless these substituents are first protected. One such class of reactive substituents are the active hydrogen containing substituents. The term "active hydrogen containing substituent" as used herein refers to a substituent which contains a reactive hydrogen atom. Examples of such substituents include but are not limited to hydroxy, amino, imino, carboxy (including carboxylato), carbamoyl, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and primary and secondary amine substituents in view of their high reactivity. Carboxyl, sulfo and the like (i.e. acidic) substituents may require additional base. Other reactive substituents include trimethylsilyl.

According to this aspect of the invention there is provided a process for preparing an organoboron derivative comprising reacting a diboron derivative with an olefinic or acetylenic compound having respectively at least one carbon to carbon double bond or at least one carbon to carbon triple bond, and a substituent reactive with organometallic compounds, in the presence of a Group 8–11 metal catalyst, such that a organoboronate residue is introduced on one or two of the carbon atoms of the respective double or triple bonds. Preferably the reactive substituent is an active hydrogen containing substituent.

Another embodiment of the present invention is based on the finding that when an olefinic compound containing a carbon to carbon double bond and a leaving group at an allylic position, is reacted with a diboron derivative in the presence of a Group 8–11 metal catalyst, the leaving group can be replaced by an organoboronate residue. Preferably the leaving group is an ester group.

Accordingly, in this embodiment, there is provided a process for preparing organoboron derivatives which comprises reacting an olefinic compound having a leaving group at an allylic substitution position with a diboron derivative in the presence of a Group 8–11 metal catalyst such that the leaving group is replaced with an organoboronate residue.

Some of the boron intermediates are novel and represent a further aspect of the present invention. Examples of such novel boron intermediates which may be prepared according to the present invention are listed below:

2-[(Z)-2-(5,5-Dimethyl-1,3,2-dioxaborinan-2-yl)-1,2-diphenylethenyl]-5,5-dimethyl-1,3,2-dioxaborinane.
2-[(Z)-2-(5,5-Dimethyl-1,3,2-dioxaborinan-2-yl)-1-ethyl-1-butenyl]-5,5-dimethyl-1,3,2-dioxaborinane.
2-[(Z)-2-(5,5-Dimethyl-1,3,2-dioxaborinan-2-yl)-1-phenyl-1-butenyl]-5,5-dimethyl-1,3,2-dioxaborinane.
Methyl (Z)-2,3-bis(4,4,5,5-tetramethyl-1,3,2-dioxaborolan-2-yl)-2-nonenoate.
(E)4-Phenyl-3-(4,4,5,5-tetramethyl-1,3,2-dioxaborolan-2-yl)-3-buten-2-one.
(Z)-4-Phenyl-4-(4,4,5,5-tetramethyl-1,3,2-dioxaborolan-2-yl)-3-buten-2-one.
2-[(E)-1-(1-Cyclohexen-1-yl)-2-(4,4,5,5-tetramethyl-1,3,2-dioxaborolan-2-yl)ethenyl]-4,4,5,5-tetramethyl-1,3,2-dioxaborolane.
1-[(E)-1,2-Bis(4,4,5,5-tetramethyl-1,3,2-dioxaborolan-2-yl)ethenyl]cyclohexanol.
(E)-N,N-Dimethyl-2,3-bis(4,4,5,5-tetramethyl-1,3,2-dioxaborolan-2-yl)-2-propen-1-amine.
(E)-3-Ethyl-1,2-bis(4,4,5,5-tetramethyl-1,3,2-dioxaborolan-2-yl)-1-penten-3-amine.
(E)-N,N-Di(2-propynyl)-2,3-bis(4,4,5,5-tetramethyl-1,3,2-dioxaborolan-2-yl)-2-propen-1-amine.
4,4,5,5-Tetramethyl-2-[3-(4,4,5,5-tetramethyl-1,3,2-dioxaborolan-2-yl)bicyclo[2.2.1]hept-2-yl]-1,3,2-dioxaborolane.
4,4-Dimethyl-3-(4,4,5,5-tetramethyl-1,3,2-dioxaborolan-2-yl)cyclohexanone.
4,4-Dimethyl-3-(4,4,5,5-tetramethyl-1,3,2-dioxaborolan-2-yl)cyclohexanone.
4-Phenyl-4-(4,4,5,5-tetramethyl-1,3,2-dioxaborolan-2-yl)-2-butanone.
4-Phenyl-4-(4,4,5,5-tetramethyl-1,3,2-dioxaborolan-2-yl)-2-butanone.
4,4,5,5-Tetramethyl-2-[4-(4,4,5,5-tetramethyl-1,3,2-dioxaborolan-2-yl)-2-cyclohexen-1-yl]-1,3,2-dioxaborolane.
(Z)-1,5-Diphenyl-5-(4,4,5,5-tetramethyl-1,3,2-dioxaborolan-2-yl)-1-penten-3-one.
3-Phenyl-3-(4,4,5,5-tetramethyl-1,3,2-dioxaborolan-2-yl)propanal.
4,4,5,5-Tetramethyl-2-[8-(4,4,5,5-tetramethyl-1,3,2-dioxaborolan-2-yl)-2,4,6-cyclooctatrien-1-yl]-1,3,2-dioxaborolane.

4,4,5,5-Tetramethyl-2-[6-(4,4,5,5-tetramethyl-1,3,2-dioxaborolan-2-yl)-2,4,7-cyclooctatrien-1-yl]-1,3,2-dioxaborolane.

4,4,5,5-Tetramethyl-2-[8-(4,4,5,5-tetramethyl-1,3,2-dioxaborolan-2-yl)-4-cycloocten-1-yl]-1,3,2-dioxaborolane.

4,4,5,5-Tetramethyl-2-[9-(4,4,5,5-tetramethyl-1,3,2-dioxaborolan-2-yl)tricyclo[5.2.1.02,6]dec-3-en-8-yl]-1,3,2-dioxaborolane.

4,4,5,5-Tetramethyl-2-[3-(4,4,5,5-tetramethyl-1,3,2-dioxaborolan-2-yl)tricyclo[5.2.1.02,6]dec-8-en-4-yl]-1,3,2-dioxaborolane.

4,4,5,5-Tetramethyl-2-(4-methylcyclohexyl)-1,3,2-dioxaborolane.

4,4,5,5-Tetramethyl-2-(3-methylcyclohexyl)-1,3,2-dioxaborolane.

4,4,5,5-Tetramethyl-2-[(E)-2-(4,4,5,5-tetramethyl-1,3,2-dioxaborolan-2-yl)-1-octen-7-ynyl]-1,3,2-dioxaborolane.

4,4,5,5-Tetramethyl-2-[(1E,7E)-2,7,8-tris(4,4,5,5-tetramethyl-1,3,2-dioxaborolan-2-yl)-1,7-octadienyl]-1,3,2-dioxaborolane.

2-[(Z)-1-Butyl-2-(4,4,5,5-tetramethyl-1,3,2-dioxaborolan-2-yl)-1-octen-3-ynyl]-4,4,5,5-tetramethyl-1,3,2-dioxaborolane.

2-[(1Z,3Z)-1-Butyl-2,3,4-tris(4,4,5,5-tetramethyl-1,3,2-dioxaborolan-2-yl)-1,3-octadienyl]-4,4,5,5-tetramethyl-1,3,2-dioxaborolane.

2-[(Z)-2-(4H-1,3,2-Benzodioxaborinin-2-yl)-1,2-diphenylethenyl]-4H-1,3,2-benzodioxaborinine.

2-[(Z)-1,2-Diphenyl-2-(4,4,6-trimethyl-1,3,2-dioxaborinan-2-yl)ethenyl]-4,4,6-trimethyl-1,3,2-dioxaborinane.

2-[(Z)-2-(5,5-Diethyl-1,3,2-dioxaborinan-2-yl)-1,2-diphenylethenyl]-5,5-diethyl-1,3,2-dioxaborinane.

(2-{(Z)-2-[4-(Phenoxymethyl)-1,3,2-dioxaborolan-2-yl]-1,2-diphenylethenyl}-1,3,2-dioxaborolan-4-yl)methyl phenyl ether.

(1S,2S,6R,8S)-4-{(Z)-1,2-diphenyl-2-[(1R,2R,6S,8S)-2,9,9-trimethyl-3,5-dioxa-4-boratricyclo[6.1.1.02,6]dec-4-yl]ethenyl}-2,9,9-trimethyl-3,5-dioxa-4-boratricyclo[6.1.1.02,6]decane.

(3aR,6aS)-2-{(Z)-2-[(3aR,6aS)Tetrahydro-3aH-cyclopenta[d][1,3,2]dioxaborol-2-yl]-1,2-diphenylethenyl}tetrahydro-3aH-cyclopenta[d][1,3,2]dioxaborole.

(3aR,6aS)-2-{(Z)-2-[(3aR,6aS)Tetrahydrofuro[3,4-d][1,3,2]dioxaborol-2-yl]-1,2-diphenylethenyl}tetrahydrofuro[3,4-d][1,3,2]dioxaborole.

2-[(Z)-1,2-Diphenyl-2-(4-phenyl-1,3,2-dioxaborolan-2-yl)ethenyl]-4-phenyl-1,3,2-dioxaborolane.

(3aR,7aS)-2-{(Z)-2-[(3aR,7aS)Hexahydro-1,3,2-benzodioxaborol-2-yl]-1,2-diphenylethenyl}hexahydro-1,3,2-benzodioxaborole.

In yet another aspect, there is provided a process for preparing an organic boronic acid derivative which comprises reacting an olefinic compound having a leaving group at an allylic substitution position and a substituent reactive with organometallic compounds with a diboron derivative in the presence of a Group 8–11 metal catalyst, such that the leaving group is substituted with an organoboronate residue.

As used herein, the term "leaving group" refers to a chemical group which is capable of being displaced by an organoboronate residue. Suitable leaving groups are apparent to those skilled in the art and include halogen and halogen-like substituents, as well as ester groups.

The term "allylic substitution position" as used herein refers to a position on the olefinic compound at which substitution with an organoboronate residue is desired and which is located on a carbon atom which is directly next to a carbon atom which is part of an olefinic carbon to carbon double bond.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-ethylpentyl, 1-methylpentyl, 2-methylpentyl, 3-methylpentyl, 1,1-dimethylbutyl, 2,2-imethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a term such as "heterocyclicalkenoyl", "heterocycloxy"or "haloheterocyclyl" refer to aromatic, pseudo-aromatic and non-aromatic rings or ring systems which contain one or more heteroatoms selected from N, S, O and P and which may be optionally substituted. Preferably the rings or ring systems have 3 to 20 carbon atoms. The rings or ring systems may be selected from those described above in relation to the definition of "aromatic compound(s)".

The term "aryl" as used herein on its own or as part of a group such as "haloaryl" and "aryloxycarbonyl" refers to aromatic and pseudo-aromatic rings or ring systems composed of carbon atoms, optionally together with one or more heteroatoms. Preferably the rings or ring systems have between 3 and 20 carbon atoms. The rings or ring systems may be optionally substituted and may be selected from those described above in relation to the definition of "aromatic compound(s)".

The term "Group 8–11 metal catalyst" as used herein refers to a catalyst comprising a metal of Groups 8–11 of the periodic table described in Chemical and Engineering News, 63(5), 27, 1985. Examples of such metals include Ni, Pt and Pd. Preferably the catalyst is a platinum catalyst, although analogous catalysts of other Group 8–11 metals may also be used. The Group 8–11 metal catalyst may be a platinum complex. Examples of suitable platinum catalysts include but are not limited to $Pt(dba)_2$, $Pt(PPh_3)_2Cl_2$, $PtCl_2$, $Pt(OAc)_2$, $PtCl_2(dppf)CH_2Cl_2$, $Pt(PPh_3)_4$ and related catalysts which are complexes of phosphine ligands, (such as $(Ph_2P(CH_2)_nPPh_2)$ where n is 2 to 4, $P(o\text{-tolyl})_3$, $P(i\text{-Pr})_3$, $P(\text{cyclohexyl})_3$, $P(o\text{-MeOPh})_3$, $P(p\text{-MeOPh})_3$, dppp, dppb, TDMPP, TTMPP, TMPP, TMSPP and related water soluble phosphines), related ligands (such as triarylarsine, triarylantimony, triarylbismuth), phosphite ligands (such as $P(OEt)_3$, $P(O\text{-p-tolyl})_3$, $P(O\text{-o-tolyl})_3$ and $P(O\text{-iPr})_3$) and other suitable ligands including those containing P and/or N atoms for co-ordinating to the platinum atoms, (such as for example pyridine, alkyl and aryl substituted pyridines, 2,2'-bipyridyl, alkyl substituted 2,2'-bipyridyl and bulky secondary or tertiary amines), and other simple platinum salts either in the presence or absence of ligands. The platinum catalysts include platinum and platinum complexes supported or tethered on solid supports, such as platinum on carbon, as well as platinum black, platinum clusters and platinum clusters containing other metals.

Examples of suitable palladium catalysts include but are not limited to $Pd_3(dba)_3$, $PdCl_2$, $Pd(OAc)_2$, $PdCl_2(dppf)CH_2Cl_2$, $Pd(PPh_3)_4$ and related catalysts which are complexes of phosphine ligands, (such as $(Ph_2P(CH_2)_nPPh_2)$ where n is 2 to 4, $P(o\text{-tolyl})_3$, $P(i\text{-Pr})_3$, $P(\text{cyclohexyl})_3$, $P(o\text{-MeOPh})_3$, $P(p\text{-MeOPh})_3$, dppp, dppb, TDMPP, TTMPP, TMPP, TMSPP and related water soluble phosphines), related ligands (such as triarylarsine, triarylantimony, triarylbismuth), phosphite ligands (such as $P(OEt)_3$, $P(O\text{-p-tolyl})_3$, $P(O\text{-o-tolyl})_3$ and $P(O\text{-iPr})_3$) and other suitable ligands including those containing P and/or N atoms for co-ordinating to the palladium atoms, (such as for example pyridine, alkyl and aryl substituted pyridines, 2,2'-bipyridyl, alkyl substituted 2,2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters and palladium clusters containing other metals and palladium in porous glass as described in J. Li, A. W-H. Mau and C. R. Strauss, Chemical Communications, 1997, p1275. The same or different Group 8–11 metal catalysts may be used to catalyse different steps in the process. The Group 8–11 metal catalyst may also be selected from those described in U.S. Pat. No. 5,686,608. In certain reactions there are advantages in using ligands with altered basicity and/or steric bulk. Examples of suitable Ni catalysts include nickel black, Raney nickel, nickel on carbon and nickel clusters or a nickel complex. Examples of other suitable Group 8–11 metal catalysts include those of Au, Rh, Ru, Fe, Co, Zn, Hg, Ag, Os, Ir and analogous complexes of these metals etc. Preferred catalysts are those that readily undergo oxidative addition and reductive elimination. One skilled in the art would be able to select a suitable catalyst on this basis. Catalysts of platinum are preferred. The Group 8–11 metal catalyst may additional contain other metals.

The process may be performed in any suitable solvent or solvent mixture. Examples of such solvents include lower alcohols, and their esters with the lower aliphatic carboxylic acids, lower aliphatic ketones, cyclic and the lower secondary and tertiary amines, amides of the lower aliphatic carboxylic acids and lower aliphatic secondary amines, DMSO, aromatic or aliphatic hydrocarbons, nitromethane, acetonitrile, benzonitrile, ethers, polyethers, cyclic ethers, lower aromatic ethers, and mixtures thereof, including mixtures with other solvents.

Preferred solvents include protic solvents such as methanol, ethanol, isopropanol and n-butanol, and non-protic solvents such as n-heptane, acetonitrile, acetone, DMSO, DMF, dioxane, DME, diethyl ether, THF, toluene or mixtures thereof with other solvents. Exclusion of water from the solvents is generally not essential and in some cases the presence of water is preferred. The addition of further diboron derivative may be useful when the solvents are not anhydrous.

It has been generally accepted that reactions of diboron derivatives should be conducted in the absence of air. However it has been surprisingly found that some reactions of diboron derivatives with olefinic or acetylenic compounds can be conducted in the presence of air. The presence of air/oxygen has been found to promote or increase the rate of the reaction, giving more product in a shorter time period. Other promoters may also be used to provide this effect. This is an important finding as the requirement for an inert atmosphere can present difficulties for commercial scale up and substantially increase the manufacturing costs. The present findings that reactions between diboron derivatives and olefinic or acetylenic compounds can precede efficiently in the presence of both air and moisture substantially increases the commercial potential of these reactions.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of −100 to 250° C. In a preferred embodiment the process is performed at a temperature between 0 and 120° C., more preferably between 0 and 80° C., and most preferably between 40 and 80° C.

The term "suitable base" as used herein refers to a basic compound which, when present in the reaction mixture, is capable of catalysing, promoting or assisting reaction between reactants. In particular a suitable base is required to catalyse the reaction between the organoboron derivative and the organic compound. A suitable base may also be added to the reaction medium to alter the products of the reaction of the diboron derivative with the olefinic or acetylenic compound. For example, the addition of base may result in a product with one organoboronate residue at one carbon atom of the relevant bond, rather than at both. Examples of bases which are suitable for catalysing the reaction of the organoboron derivative and the organic compound include aryl and alkyl carboxylates (for example potassium acetate), fluorides, hydroxides and carbonates of Li, Na, K, Rb, Cs, ammonium, alkylammonium, Mg, Ca, & Ba; phosphates and arylphosphates of Li, Na, K, Rb and Cs; phosphate esters (eg. $C_6H_5OP(O)(ONa)_2$) of Li, Na, K, Rb, Cs, ammonium and alkylammonium; phenoxides of Li, Na, K, Rb and Cs; alkoxides of Li, Na, K, Rb and Cs; and thallium hydroxide. Some of these bases may be used in conjunction with a phase transfer reagent, such as for example tetraalkylammonium salts or the crown ethers. The weaker of these bases may require some heating to allow the coupling reaction to proceed. Examples of bases suitable for decomposing excess diboron derivative and/or catalysing reaction of the organoboron intermediate with the organic compound generally without much heating include the stronger bases listed above, including cesium carbonate, potassium carbonate, potassium phosphate and alkali metal hydroxides.

In a further aspect of the invention there is provided a process for preparing an organoboron intermediate, comprising reacting a diboron derivative with an olefinic compound having at least one carbon to carbon double bond or an acetylenic compound having at least one carbon to carbon triple bond in the presence of a Group 8–11 metal catalyst such that an organoboronate residue is introduced on one or two of the carbon atoms of the respective double or triple bond.

A first step in the purification of the intermediate so formed may be the decomposition of any excess diboron derivative by the use of water, water and suitable base, or by the use of a mild oxidising agent.

In a further aspect of the invention, there is provided a process for the preparation of an organo boronic acid by hydrolysing the organoboron intermediate as hereinbefore described using established procedures. The ease of hydrolysis is a function of the diboronic ester used. Some alkene borate intermediates are more amenable to hydrolysis than those derived from bis(pinacolato)diboron.

The present invention provides a novel route to some chiral compounds. In this regard the conversion of a double bond having a substituent on one or both ends, or being part of a cyclic structure, to a single bond produces new chiral centres. The stereoselective nature of the reaction under certain conditions of the olefinic compound with the diboron derivative can result in products with a high enantiomeric excess, especially if a chiral diboron derivative is used having an enantiomeric excess of at least one enantiomer over another. Similarly it is possible to react the diboron derivatives with acetylenic compounds to produce particular geometric isomers, which may also be chiral if chiral diboron derivatives are used. Chiral intermediates and end products (having an enantiomeric excess of at least one enantiomer over another) may be produced by the use of chiral borate esters. For example the chirality of an organoboron intermediate can be transferred to a coupled product.

According to another aspect, the present invention provides a process for covalently coupling organic compounds which comprises reacting an organoboron derivative prepared as hereinbefore described with an organic compound having a halogen or halogen-like substituent at a coupling position in the presence of a Group 8–11 metal catalyst and a suitable base.

In a further aspect there is provided a "one-pot" procedure for covalently coupling organic compounds comprising reacting:

(i) an olefinic organic compound; or
(ii) an acetylenic compound with a diboron derivative as hereinbefore defined to form an organoboron intermediate and reacting the organoboron derivative in situ with an organic compound having a halogen or halogen-like substituent at a coupling position in the presence of a Group 8–11 metal catalyst and a suitable base to form a direct bond between the coupling position and a carbon atom of the organoboron derivative to which the organoboronate residue is attached.

The process according to the present invention is applicable to chemistry on solid polymer support or resin bead in the same manner as conventional chemistry is used in combinatorial chemistry and in the preparation of chemical libraries. Thus a suitable organic compound having a halogen or halogen-like substituent at a coupling position which is chemically linked via a linking group to a polymer surface may be reacted with an organoboron derivative in the presence of a Group 8–11 metal catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface. The process is also possible using the alternative strategy of reacting: (i) an olefinic organic compound, or (ii) an acetylenic compound, linked to a polymer surface with a diboron derivative as previously described to form an organoboron derivative chemically linked to the polymer surface. This derivative may then be reacted with an organic compound having a halogen or halogen-like substituent at a coupling position in the presence of a Group 8–11 metal catalyst and a suitable base to prepare the coupled product chemically linked to the polymer. Excess reactants and by-products may be removed by suitable washing and the coupled product may be isolated by chemically cleaving the link to the polymer.

The term "linking group" as used herein refers to any chain of atoms linking one organic group to another. Examples of linking groups include polymer chains, optionally substituted alkylene group and any other suitable divalent group.

It is also possible to prepare polymers by reaction of organoboron derivatives having more than one organoboronate residue with organic compounds having more than one halogen or halogen-like substituent. If the organic compound has three or more halogen or halogen-like substituents which react with the organoboron derivative and/or the organoboron derivative has three or more organoboronate residues then it is possible to prepare dendritic molecules in accordance with the process of the present invention.

The organic compounds which are to be coupled may be separate molecules or may be linked together such that the organoboron derivative formed after reaction with the diboron derivative is able to react at a coupling position located elsewhere in the molecule so as to provide for an intramolecular reaction, such as a ring closure reaction.

The process according to the invention is also useful for the preparation of reactive intermediates which are capable of taking part in further reactions or rearrangements. These reactive intermediates may be the organoboron derivatives or the coupled products. For example, some derivatives may take part in one or more of the palladium catalysed reactions of organoboron compounds described by Miyaura and Suzuki in Chem. Rev. 1995, 95 2457–2483.

The process according to the present invention allows the linking of organic compounds in mild conditions and avoids the use of expensive, difficult to remove and/or toxic reagents and solvents. In this regard boron and boron compounds are generally non-toxic. It also allows the reaction to be performed in the presence of air and moisture. The reactions may also be performed in relatively cheap solvents such as methanol and ethanol and, in view of the improved control over the reaction steps, it is envisaged that it would be possible to perform the reactions on an industrial scale. The process also allows the linking of organic compounds which contain active hydrogen substituents without the need to protect those substituents during the reaction.

The following Examples are provided to illustrate some preferred embodiments of the invention. However, it is to be understood that the following description is not to supersede the generality of the invention previously described.

EXAMPLES

Example 1

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane

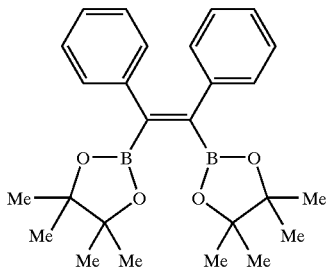

The pinacol ester of diboronic acid (0.254 g; 1.0 mmole), diphenylacetylene (0.178 g; 1.0 mmoles) and tetrakis (triphenylphosphine)platinum (0.037 g; 0.030 mmoles) were placed in a Schlenk tube open to the atmosphere. Toluene (5 mL, dried over 4 Å molecular sieve) was added, and the open tube was heated at 80° C. with stirring for 10 hours. GC analysis showed a peak corresponding to the diboronic ester of diphenylacetylene at 17.0 minutes as the principal product (94%), together with a trace of the monoboronic ester (<0.5%).

An identical reaction carried out under an atmosphere of nitrogen gave, after 10 hours, unreacted starting material, together with a peak corresponding to 50% conversion of starting material to the diboronic ester of diphenylacetylene at 17.0 minutes as the principal product.

Example 2

2-[(Z)-1,2-Diphenylethenyl]-4,4,5,5-tetramethyl-1,3,2-dioxaborolane

2-[(Z)-1,2-Diphenyl-2-(4,4,5,5-tetramethyl-1,3,2-dioxaborolan-2-yl)ethenyl]-4,4,5,5-tetramethyl-1,3,2-dioxabbrolane

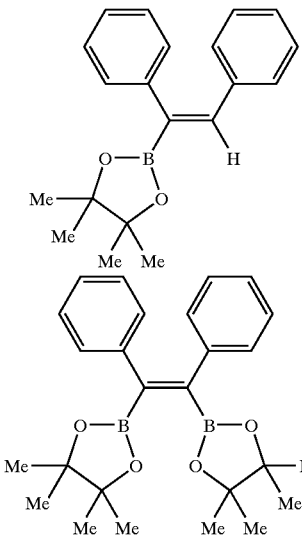

The pinacol ester of diboronic acid (0.254 g; 1.0 mmole), diphenylacetylene (0.196 g; 1.1 mmoles), tetrakis (triphenylphosphine)platinum (0.037 g; 0.030 mmoles) and potassium acetate (0.196 g; 2.0 mmoles) were placed in a Schlenk tube under an atmosphere of nitrogen. DMF (5 mL, dried over 4 Å molecular sieve) was added under argon, and the tube was heated at 80° C. with stirring for 5 hours. GC analysis showed product peaks corresponding to cis-stilbene at 7.9 minutes (4%), the monoboronic ester of diphenylacetylene at 14.0 minutes (47%) and the diboronic ester of diphenylacetylene at 17.0 minutes (44%). Heating for a further 69 hours at 80° C. gave cis-stilbene (15%) and the monoboronic ester (88%), at the expense of the diboronic ester (<2%).

Example 3

2-[(Z)-1,2-Diphenylethenyl]-4,4,5,5-tetramethyl-1,3,2-dioxaborolane

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The pinacol ester of diboronic acid (0.254 g; 1.0 mmole), diphenylacetylene (0.196 g; 1.1 mmoles), tetrakis (triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 20 hours. GC analysis confirmed effectively quantitative formation of the diboronic ester (>98%). Potassium acetate (0.196 g; 2.0 mmoles) was added, and heating was continued for a further 69 hours at 80° C. Approximately 75% of the diboronic ester underwent hydrodeboration to give the monoboronic ester.

Example 4

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane

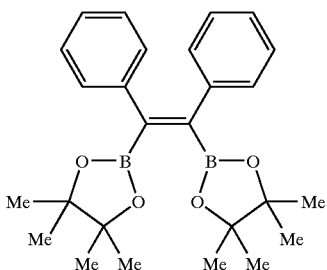

The pinacol ester of diboronic acid (0.254 g; 1.0 mmole), diphenylacetylene (0.196 g; 1.1 mmoles) and tetrakis (triphenylphosphine)palladium (0.035 g; 0.030 mmoles) were placed in a Schlenk tube under an atmosphere of nitrogen. DMF (5 mL, dried over 4 Å molecular sieve) was added under argon, and the tube was heated at 80° C. with stirring for 20 hours. GC analysis showed a peak corresponding to the diboronic ester of diphenylacetylene at 17.0 minutes as the principal product (>97%).

Example 5

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The pinacol ester of diboronic acid (0.254 g; 1.0 mmole), diphenylacetylene (0.196 g; 1.1 mmoles) and cis-bis (triphenylphosphine)dichloroplatinum(II) (0.024 g, 0.030 mmoles) were placed in a Schlenk tube under an atmosphere of nitrogen. DMF (5 mL, dried over 4 Å molecular sieve) was added under argon, and the tube was heated at 80° C. with stirring for 91 hours. GC analysis showed a peak corresponding to the diboronic ester of diphenylacetylene at 17.0 minutes (23%).

Example 6

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane

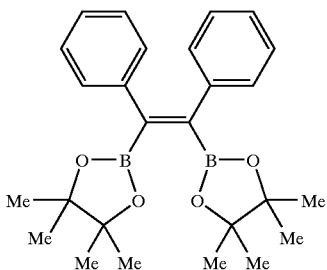

The pinacol ester of diboronic acid (0.254 g; 1.0 mmole), diphenylacetylene (0.196 g; 1.1 mmoles) and tetrakis (triphenylphosphine)platinum (0.037 g; 0.030 mmoles) were placed in a Schlenk tube under an atmosphere of nitrogen. THF (5 mL) was added under argon, and the tube was heated at 80° C. with stirring for 5 hours. GC analysis showed a peak corresponding to the diboronic ester of diphenylacetylene at 17.0 minutes as the principal product (>95%).

Example 7

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using dioxane (5 mL) as the solvent in place of THF. The diboronic ester of diphenylacetylene was the principal product (>95%).

Example 8

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using dichloromethane (5 mL) as the solvent in place of THF. The reaction was allowed to proceed at 80° C. for 22 hours. The diboronic ester of diphenylacetylene was the principal product (>95%).

Example 9

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using toluene (5 mL, dried over 4 Å molecular sieve) as the solvent in place of THF. The diboronic ester of diphenylacetylene was the principal product (>95%).

Example 10

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using acetonitrile (5 mL, dried over 4 Å molecular sieve) as the solvent in place of THF. After 1.5 hours reaction time, the diboronic ester of diphenylacetylene was the principal product (>95%).

Example 11

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using n-heptane (5 mL, dried over 4 Å molecular sieve) as the solvent in place of THF. The catalyst appeared to be largely insoluble in this medium. The reaction was allowed to proceed at 80° C. for 20 hours. The diboronic ester of diphenylacetylene was the principal product (>92%).

Example 12

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using acetone (5 mL) as the solvent in place of THF. The reaction was allowed to proceed at 80° C. for 20 hours. The diboronic ester of diphenylacetylene was the principal product (>95%).

Example 13

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane The reaction described in Example 6 was carried out using n-butanol (5 mL) as the solvent in place of THF. After 1.5 hours at 80° C., gc analysis showed the diboronic ester of diphenylacetylene as the principal product (88%), together with the monoboronic ester (5%). Heating for an additional 18 hours at 80° C. gave the diboronic ester of diphenylacetylene (66%), the monoboronic ester (19%) and cis-stilbene (4%).

Example 14

4,4,5,5-Tetramethyl-2-[(Z)-1-phenyl-2-(4,4,5,5-tetramethyl-1,3,2-dioxaborolan-2-yl)-1-butenyl]-1,3,2-dioxaborolane 2-[(1Z,3Z)-2,3-Diethyl-1,4-diphenyl-4-(4,4,5,5-tetramethyl-1,3,2-dioxaborolan-2-yl)-1,3-butadienyl]-4,4,5,5-tetramethyl-1,3,2-dioxaborolane 2-[(1Z,3Z)-1-Ethyl-2,3-diphenyl-4-(4,4,5,5-tetramethyl-1,3,2-dioxaborolan-2-yl)-1,3-dienyl]-4,4,5,5-tetramethyl-1,3,2-dioxaborolane

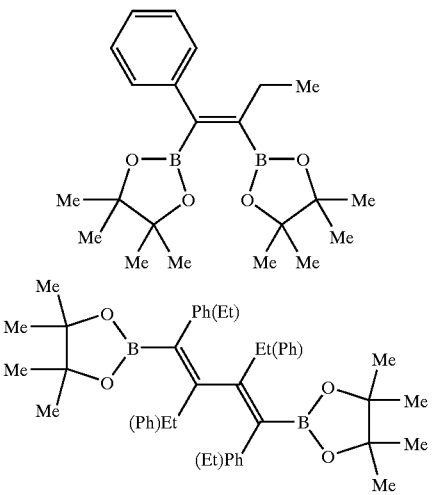

The pinacol ester of diboronic acid (0.254 g; 1.0 mmole), 1-phenylbutyne (0.143 g; 1.1 mmoles) and bis(dibenzylideneacetone)platinum Pt(dba)$_2$ (0.020 g; 0.030 mmoles) were placed in a Schlenk tube under an atmosphere of nitrogen. Toluene (5 mL, dried over 4 Å molecular sieve) was added under argon, and the tube was heated at 70° C. with stirring for 63 hours. GC analysis showed the peak corresponding to the diboronic ester of 1-phenylbutyne at 14.2 minutes (53%), and a peak at 13.8 minutes (8S), which is shown by mass spectrometry to be an isomeric form of the diboronic ester of 1-phenylbutyne. There was also a peak at 17.8 minutes (25%), corresponding to the coupling of two monoboronate esters.

Example 15

4,4,5,5-Tetramethyl-2-[(Z)-1-phenyl-2-(4,4,5,5-tetramethyl-1,3,2-dioxaborolan-2-yl)-1-butenyl]-1,3,2-dioxaborolane

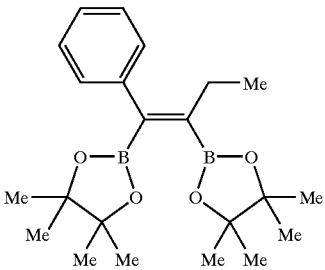

The pinacol ester of diboronic acid (0.254 g; 1.0 mmole), 1-phenyl-1-butyne (0.143 g; 1.1 mmoles) and tetrakis(triphenylphosphine)platinum (0.037 g; 0.030 mmoles) were placed in a Schlenk tube open to the atmosphere. Toluene (5 mL, dried over 4 Å molecular sieve) was added, and the open tube was heated at 80° C. with stirring for 2 hours. GC analysis showed a peak corresponding to the diboronic ester of 1-phenyl-1-butyne at 14.2 minutes as the principal product (>95%).

An identical reaction mixture that was run under an atmosphere of nitrogen gave, after 2 hours, unreacted starting material, together with a peak corresponding to 50% conversion of starting material to the diboronic ester of 1-phenyl-1-butyne at 14.2 minutes as the principal product:

Example 16

2-[(Z)-1-Ethyl-2-(4,4,5,5-tetramethyl-1,3,2-dioxaborolan-2-yl)-1-butenyl]-4,4,5,5-tetramethyl-1,2-oxaborolan-3-ol 2-[(Z)-1-Ethyl-1-butenyl]-4,4,5,5-tetramethyl-1,2-oxaborolan-3-ol

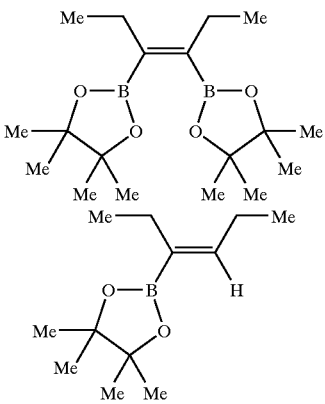

The pinacol ester of diboronic acid (0.254 g; 1.0 mmole), 3-hexyne (0.094 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 3.3 hours. GC analysis showed the presence of the product diboronic ester at 10.9 minutes as the principal product (>98%). Potassium carbonate (0.200 g, 2.0 mmoles) was added under argon. The tube was heated for a further 66 hours at 80° C., and gc analysis showed the presence of unchanged diboronic ester at (30%) and the monoboronic ester at 3.7 minutes (66%) arising from monohydrodeboration of the diboronic ester.

Example 17

2-[(Z)-2-(5,5-Dimethyl-1,3,2-dioxaborinan-2-yl)-1, 2-diphenylethenyl]-5,5-dimethyl-1,3,2-dioxaborinane

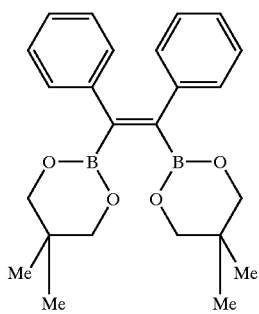

The neopentyl ester of diboronic acid (0.226 g; 1.0 mmole), diphenylacetylene (0.196 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 100° C. with stirring for 72 hours. GC analysis showed peaks corresponding to the diboronic ester of diphenylacetylene at 18.2 minutes (91%), and the monoboronic ester at 15.0 minutes (7%) as the principal products.

Example 18

2-[(Z)-2-(5,5-Dimethyl-1,3,2-dioxaborinan-2-yl)-1-ethyl-1-butenyl]-5,5-dimethyl-1,3,2-dioxaborinane

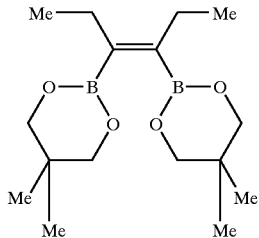

The neopentyl ester of diboronic acid (0.226 g; 1.0 mmole), 3-hexyne (0.094 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 100° C. with stirring for 4 hours. GC analysis showed a peak corresponding to the diboronic ester of 3-hexyne at 12.2 minutes (86%).

Example 19

2-[(Z)-2-(5,5-Dimethyl-1,3,2-dioxaborinan-2-yl)-1-phenyl-1-butenyl]-5,5-dimethyl-1,3,2-dioxaborinane

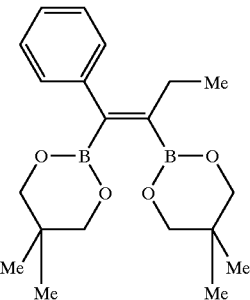

The neopentyl ester of diboronic acid (0.226 g; 1.0 mmole), 1-phenyl butyne (0.143 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 70° C. with stirring for 86 hours. GC analysis showed a peak corresponding to the diboronic ester of 1-phenyl butyne at 15.7 minutes (81%).

Example 20

Methyl (Z)-2,3-bis(4,4,5,5-Tetramethyl-1,3,2-dioxaborolan-2-yl)-2-nonenoate

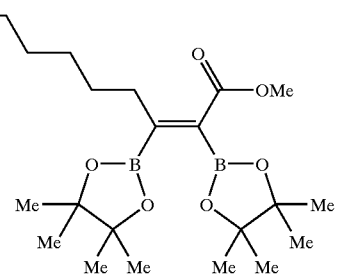

The pinacol ester of diboronic acid (0.254 g; 1.0 mmole), methyl-2-nonynoate (0.185 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 18 hours. GC analysis showed the presence of the product diboronic ester at 15.6 minutes as the principal product (98%). Potassium acetate (0.160 g, 1.6 mmoles) was added under argon. The tube was heated for a further 18 hours at 80° C., and gc analysis showed the presence of one principal product at 11.0 minutes (>90%) corresponding to a monoboronic ester arising from hydrodeboration.

Example 21

(E)-4-Phenyl-3-(4,4,5,5-tetramethyl-1,3,2-dioxaborolan-2-yl)-3-buten-2-one (Z)-4-Phenyl-4-(4,4,5,5-tetramethyl-1,3,2-dioxaborolan-2-yl)-3-buten-2-one

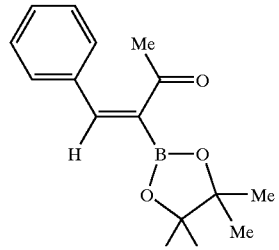

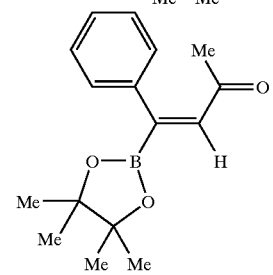

The pinacol ester of diboronic acid (0.254 g; 1.0 mmole), 4-phenyl-3-butyne-2-one (0.150 g; 1.0 mmole) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 42 hours. GC analysis showed the product monoboronic esters at 11.5 minutes (11%) and 11.9 minutes (23%).

Example 22

2-[(E)-1-(1-Cyclohexen-1-yl)-2-(4,4,5,5-tetramethyl-1,3,2-dioxaborolan-2-yl)ethenyl]-4,4,5,5-tetramethyl-1,3,2-dioxaborolane

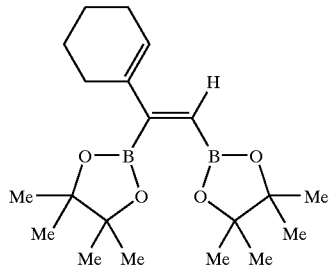

The pinacol ester of diboronic acid (0.254 g; 1.0 mmole), 1-ethynylcyclohexene (0.126 g; 1.2 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 50 hours. GC analysis showed a peak corresponding to the product diboronic ester at 15.2 minutes (78%).

Example 23

1-[(E)-1,2-bis(4,4,5,5-Tetramethyl-1,3,2-dioxaborolan-2-yl)ethenyl]cyclohexanol

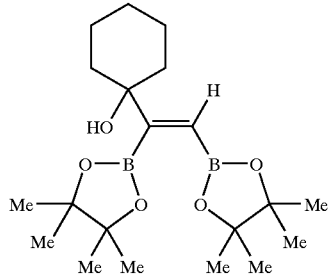

The pinacol ester of diboronic acid (0.254 g; 1.0 mmole), 1-ethynyl-cyclohexan-1-ol (0.140 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 120 hours. GC analysis showed a peak corresponding to the product diboronic ester at 15.6 minutes (94%).

Example 24

(E)-N,N-Dimethyl-2,3-bis(4,4,5,5-tetramethyl-1,3,2-dioxaborolan-2-yl)-2-propen-1-amine Or N-[(E)-2,3-bis(4,4,5,5-Tetramethyl-1,3,2-dioxaborolan-2-yl)-2-propenyl]-N,N-dimethylamine

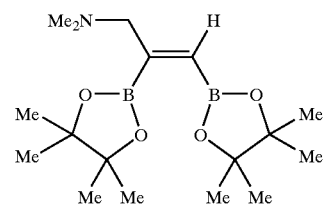

The pinacol ester of diboronic acid (0.254 g; 1.0 mmole), 1-dimethylamino-2-propyne (0.095 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 48 hours. GC analysis showed a peak corresponding to the product diboronic ester at 10.8 minutes (85%).

Example 25

(E)-3-Ethyl-1,2-bis(4,4,5,5-tetramethyl-1,3,2-dioxaborolan-2-yl)-1-penten-3-amine Or (E)-1,1-Diethyl-2,3-bis(4,4,5,5-tetramethyl-1,3,2-dioxaborolan-2-yl)-2-propenylamine

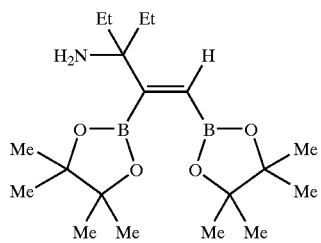

The pinacol ester of diboronic acid (0.254 g; 1.0 mmole), 3-amino-3-ethyl-1-pentyne (0.135 g; 1.2 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 48 hours. GC analysis showed a peak corresponding to the product diboronic ester at 13.1 minutes (38%), and a monoboronic ester at 7.6 minutes (60%).

Example 26

(E)-N,N-Di(2-Propynyl)-2,3-bis(4,4,5,5-tetramethyl-1,3,2-dioxaborolan-2-yl)-2-propen-1-amine Or N-[(E)-2,3-bis(4,4,5,5-Tetramethyl-1,3,2-dioxaborolan-2-yl)-2-propenyl]-N,N-di(2-propynyl)amine

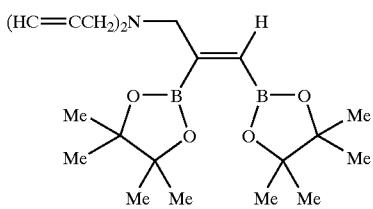

The pinacol ester of diboronic acid (0.254 g; 1.0 mmole), tripropargylamine (0.144 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 424 hours. GC analysis showed a peak corresponding to the product diboronic ester at 13.8 minutes (63%).

Example 27

4,4,5,5-Tetramethyl-2-[3-(4,4,5,5-tetramethyl-1,3,2-dioxaborolan-2-yl)bicyclo[2.2.1]hept-2-yl]-1,3,2-dioxaborolane

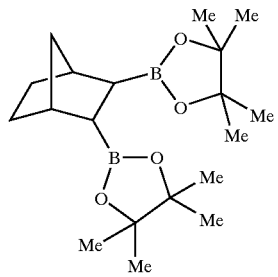

The pinacol ester of diboronic acid (0.254 g; 1.0 mmole), norbornylene (0.188 g; 2.0 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 92 hours, and then at 100° C. for 73 hours. GC analysis showed a peak corresponding to the diboronic ester at 12.9 minutes (>95%).

Example 28

4,4,5,5-Tetramethyl-2-[3-(4,4,5,5-tetramethyl-1,3,2-dioxaborolan-2-yl)bicyclo[2.2.1]hept-2-yl]-1,3,2-dioxaborolane The pinacol ester of diboronic acid (0.254 g; 1.0 mmole), norbornylene (0.188 g; 2.0 mmoles) and tris(dibenzylideneactone)dipalladium (0.027 g, 0.030 mmoles) were placed in a Schlenk tube under an atmosphere of nitrogen. DMF (5 mL, dried over 4 Å molecular sieve) was added under argon, and the tube was heated at 80° C. with stirring for 92 hours. GC analysis showed a peak corresponding to the diboronic ester at 12.9 minutes (8%).

Example 29

4,4-Dimethyl-3-(4,4,5,5-tetramethyl-1,3,2-dioxaborolan-2-yl)cyclohexanone

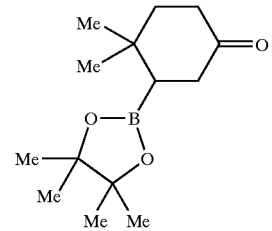

The pinacol ester of diboronic acid (0.254 g; 1.0 mmole), 4,4-dimethyl-2-cyclohexen-1-one (0.137 g; 1.1 mmoles) and bis(benzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 70° C. with stirring for 17 hours. GC analysis showed a peak corresponding to 15% conversion to the boronic ester of 4,4-dimethyl-2-cyclohexen-1-one at 9.8 minutes.

Example 30

4-Phenyl-4-(4,4,5,5-tetramethyl-1,3,2-dioxaborolan-2-yl)-2-butanone

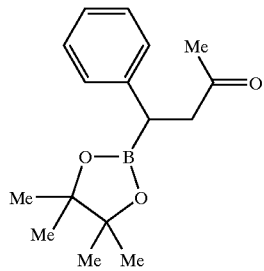

The pinacol ester of diboronic acid (0.254 g; 1.0 mmole), trans-4-phenyl-3-buten-2-one (0.161 g; 1.1 mmoles) and bis(benzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 70° C. with stirring for 17 hours. GC analysis showed the boronic ester of trans-4-phenyl-3-buten-2-one at 10.6 minutes (>95%) as the principal product.

Example 31

4-Phenyl-4-(4,4,5,5-tetramethyl-1,3,2-dioxaborolan-2-yl)-2-butanone

The pinacol ester of diboronic acid (0.254 g; 1.0 mmole), trans-4-phenyl-3-buten-2-one (0.161 g; 1.1 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 18 hours. GC analysis showed a peak corresponding to the boronic ester of trans-4-phenyl-3-buten-2-one at 10.6 minutes (>95%) as the principal product.

Example 32

2-[(Z)-1,2-Diphenyl-2-(4,4,5,5-tetramethyl-1,3,2-dioxaborolan-2-yl)ethenyl]-4,4,5,5-tetramethyl-1,3,2-dioxaborolane

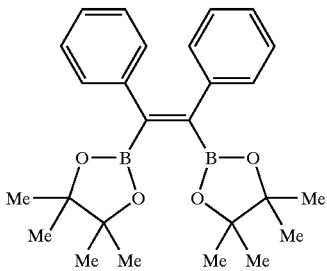

The pinacol ester of diboronic acid (0.254 g; 1.0 mmole), diphenylacetylene (0.196 g; 1.1 moles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 70° C. with stirring for 88 hours. GC analysis showed the peak corresponding to the diboronic ester of diphenylacetylene at 17.0 minutes (25%), and a peak at 16.8 minutes (48%), which was shown by mass spectrometry to be an isomer of the diboronic ester of diphenylacetylene.

Example 33

2-[(Z)-1,3-Dimethyl-4-(4,4,5,5-tetramethyl-1,3,2-dioxaborolan-2-yl)-2-butenyl]-4,4,5,5-tetramethyl-1,3,2-dioxaborolane

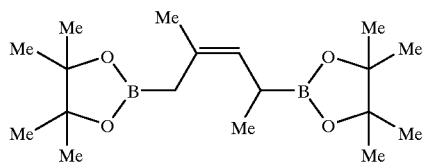

The pinacol ester of diboronic acid (0.254 g; 1.0 mmole), 2-methyl-1,3-pentadiene (0.120 g; 1.5 mmoles) and tetrakis(triphenylphosphine)platinum (0.037 g; 0.030 mmoles) were placed in a Schlenk tube under an atmosphere of nitrogen. Toluene (5 mL, dried over 4 Å molecular sieve) was added under argon, and the tube was heated at 70° C. with stirring for 63 hours. GC analysis showed a peak corresponding to the diboronic ester of 2-methyl-1,3-pentadiene at 10.1 minutes as the principal product (12% conversion).

Example 34

4,4,5,5-Tetramethyl-2-[4-(4,4,5,5-tetramethyl-1,3,2-dioxaborolan-2-yl)-2-cyclohexen-1-yl]-1,3,2-dioxaborolane

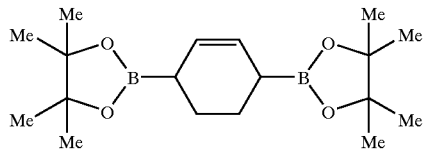

The pinacol ester of diboronic acid (0.254 g; 1.0 mmole), 1,3-cyclohexadiene (0.120 g; 1.5 mmoles) and tetrakis(triphenylphosphine)platinum (0.037 g; 0.030 mmoles) were placed in a Schlenk tube under an atmosphere of nitrogen. Toluene (5 mL, dried over 4 Å molecular sieve) was added under argon, and the tube was heated at 70° C. with stirring for 63 hours. GC analysis showed two product peaks, at 11.5 minutes (3%) and 11.7 minutes (82%). The mass spectra show very similar fragmentation patterns, and the molecular masses are consistent with the formation of two diboronic esters of cyclohexa-1,3-diene.

Example 35

4,4,5,5-Tetramethyl-2-[4-(4,4,5,5-tetramethyl-1,3,2-dioxaborolan-2-yl)-2-cyclohexen-1-yl]-1,3,2-dioxaborolane

The pinacol ester of diboronic acid (0.254 g; 1.0 mmole), 1,3-cyclohexadiene (0.120 g; 1.5 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 50° C. with stirring for 16 hours. GC analysis showed peaks at 11.5 minutes (5%) and 11.7 minutes (84%), as in example 34, together with a peak at 14.3 minutes corresponding to the 1,4-diboronic ester of benzene (1%).

Example 36

4,4,5,5-Tetramethyl-2-[(Z)-1-phenyl-2-(4,4,5,5-tetramethyl-1,3,2-dioxaborolan-2-yl)-1-butenyl]-1,3,2-dioxaborolane

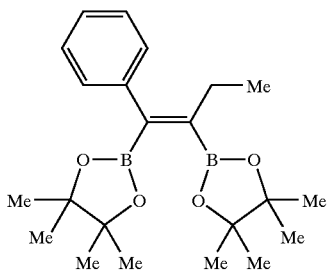

The pinacol ester of diboronic acid (0.254 g; 1.0 mmole), 1-phenylbutyne (0.143 g; 1.1 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 70° C. with stirring for 63 hours. GC analysis showed a peak corresponding to the diboronic ester of 1-phenylbutyne at 14.2 minutes (53%), together with another peak at 13.8 minutes (8%), which was shown by mass spectrometry to be an isomer of the diboronic ester of 1-phenylbutyne.

Example 37

(Z)-1,5-Diphenyl-5-(4,4,5,5-tetramethyl-1,3,2-dioxaborolan-2-yl)-1-penten-3-one

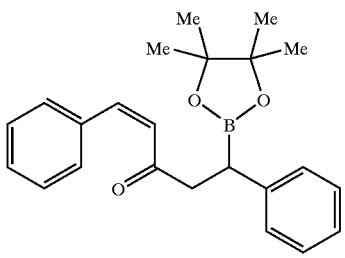

The pinacol ester of diboronic acid (0.254 g; 1.0 mmole), dibenzylideneacetone (0.257 g; 1.1 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 50° C. with stirring for 15 hours. GC analysis showed a peak corresponding to the boronic ester of dibenzylideneacetone at 18.2 minutes (68%).

Example 38

(Z)-1,5-Diphenyl-5-(4,4,5,5-tetramethyl-1,3,2-dioxaborolan-2-yl)-1-penten-3-one

The pinacol ester of diboronic acid (0.254 g; 1.0 mmole), dibenzylideneacetone (0.257 g; 1.1 mmoles) and tetrakis(triphenylphosphine)platinum (0.037 g; 0.030 mmoles) were placed in a Schlenk tube under an atmosphere of nitrogen. Toluene (5 mL, dried over 4 Å molecular sieve) was added under argon, and the tube was heated at 80° C. with stirring for 15 hours. GC analysis showed the presence of a peak corresponding to the boronic ester of dibenzylideneacetone at 18.2 minutes (30% conversion).

Example 39

3-Phenyl-3-(4,4,5,5-tetramethyl-1,3,2-dioxaborolan-2-yl)propanal

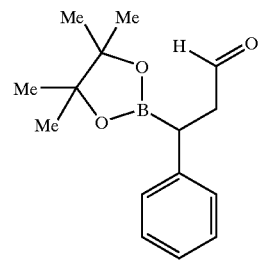

The pinacol ester of diboronic acid (0.254 g; 1.0 mmole), trans-cinnamaldehyde (0.145 g; 1.1 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 50° C. with stirring for 15 hours. GC analysis showed a peak corresponding to the boronic ester of trans-cinnamaldehyde at 10.1 minutes (37%).

Example 40

3-Phenyl-3-(4,4,5,5-tetramethyl-1,3,2-dioxaborolan-2-yl)propanal

The pinacol ester of diboronic acid (0.254 g; 1.0 mmole), trans-cinnamaldehyde (0.145 g; 1.1 mmoles) and tetrakis(triphenylphosphine)platinum (0.037 g; 0.030 mmoles) were placed in a Schlenk tube under an atmosphere of nitrogen. Toluene (5 mL, dried over 4 Å molecular sieve) was added under argon, and the tube was heated at 80° C. with stirring for 15 hours. GC analysis showed the presence of a peak corresponding to the boronic ester of trans-cinnamaldehyde at 10.1 minutes (12%).

Example 41

4,4,5,5-Tetramethyl-2-[8-(4,4,5,5-tetramethyl-1,3,2-dioxaborolan-2-yl)-2,4,6-cyclooctatrien-1-yl]-1,3,2-dioxaborolane 4,4,5,5-Tetramethyl-2-[6-(4,4,5,5-tetramethyl-1,3,2-dioxaborolan-2-yl)-2,4,7-cyclooctatrien-1-yl]-1,3,2-dioxaborolane

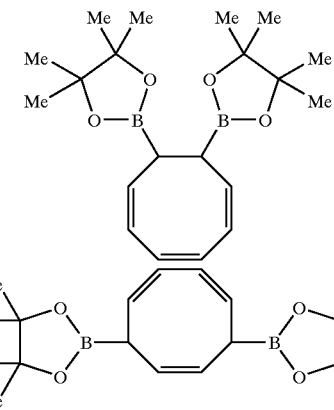

The pinacol ester of diboronic acid (0.254 g; 1.0 mmole), 1,3,5,7-cyclooctatetraene (0.114 g; 1.1 mmoles) and tetrakis (triphenylphosphine)platinum (0.037 g; 0.030 mmoles) were placed in a Schlenk tube under an atmosphere of nitrogen. Toluene (5 mL, dried over 4 Å molecular sieve) was added under argon, and the tube was heated at 50° C. with stirring for 15 hours. GC analysis showed peaks corresponding to a diboronic ester of 1,3,5,7-cycloctatetraene at 14.2 minutes (5% conversion) and a compound at 19.4 minutes (7% conversion) having a molecular mass corresponding to a diboronic ester of two coupled cycloctatetraene rings.

Example 42

4,4,5,5-Tetramethyl-2-[8-(4,4,5,5-tetramethyl-1,3,2-dioxaborolan-2-yl)-4-cycloocten-1-yl]-1,3,2-dioxaborolane

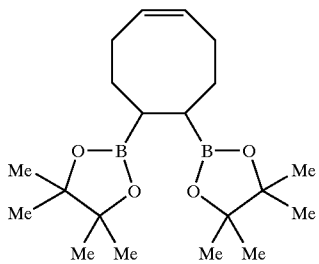

The pinacol ester of diboronic acid (0.254 g; 1.0 mmole), 1,5-octadiene (0.120 g; 1.1 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 50° C. with stirring for 22 hours, and then at 80° C. with stirring for a further 17 hours. GC analysis showed two peaks at 13.4 minutes (52%) and 13.5 minutes (8.5%), having very similar fragmentation patterns, and molecular masses consistent with diboronic esters of 1,5-octadiene.

Example 43

4,4,5,5-Tetramethyl-2-[9-(4,4,5,5-tetramethyl-1,3,2-dioxaborolan-2-yl)tricyclo[5.2.1.02,6]dec-3-en-8-yl]-1,3,2-dioxaborolane 4,4,5,5-Tetramethyl-2-[3-(4,4,5,5-tetramethyl-1,3,2-dioxaborolan-2-yl)tricyclo[5.2.1.02,6]dec-8-en-4-yl]-1,3,2-dioxaborolane

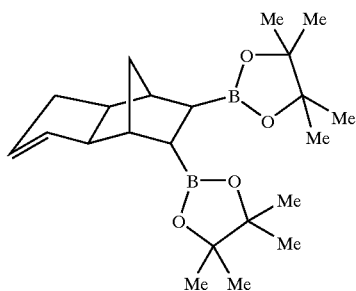

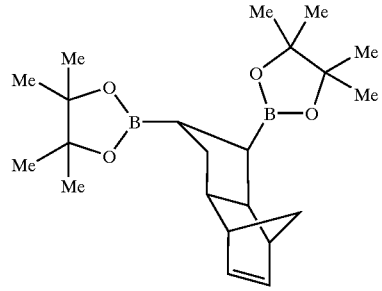

The pinacol ester of diboronic acid (0.254 g; 1.0 mmole), dicyclopentadiene (0.145 g; 1.1 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 50° C. with stirring for 17 hours. GC analysis showed a peak corresponding to a diboronic ester of dicyclopentadiene at 15.3 minutes (50%), together with a pair of peaks at 9.9 minutes (8%) and 10 minutes (7%), corresponding to two monohydrodeboration products.

Example 44

4,4,5,5-Tetramethyl-2-(4-methylcyclohexyl)-1,3,2-dioxaborolane

And 4,4,5,5-Tetramethyl-2-(3-methylcyclohexyl)-1,3,2-dioxaborolane

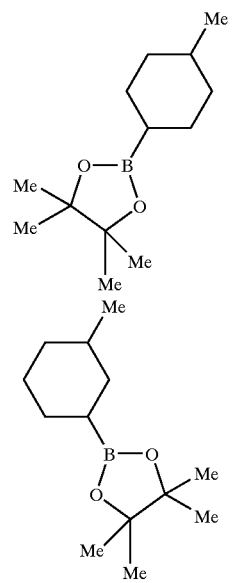

The pinacol ester of diboronic acid (0.254 g; 1.0 mmole), 4-methyl-cyclohexene (0.110 g; 1.2 mmoles) and bis(dibenzylideneacetone)platinum (0.020 g; 0.030 mmoles) were placed in a Schlenk tube under an atmosphere of nitrogen. Toluene (5 mL, dried over 4 Å molecular sieve) was added under argon, and the tube was heated at 80° C. with stirring for 232 hours. GC analysis showed a pair of peaks at 7.0 minutes (9%) and 10 minutes (5%), corresponding to two monohydrodeboration products.

Example 45

4,4,5,5-Tetramethyl-2-[(E)-2-(4,4,5,5-tetramethyl-1,3,2-dioxaborolan-2-yl)-1-octen-7-ynyl]-1,3,2-dioxaborolane 4,4,5,5-Tetramethyl-2-[(1E,7E)-2,7,8-tris(4,4,5,5-tetramethyl-1,3,2-dioxaborolan-2-yl)-1,7-octadienyl]-1,3,2-dioxaborolane

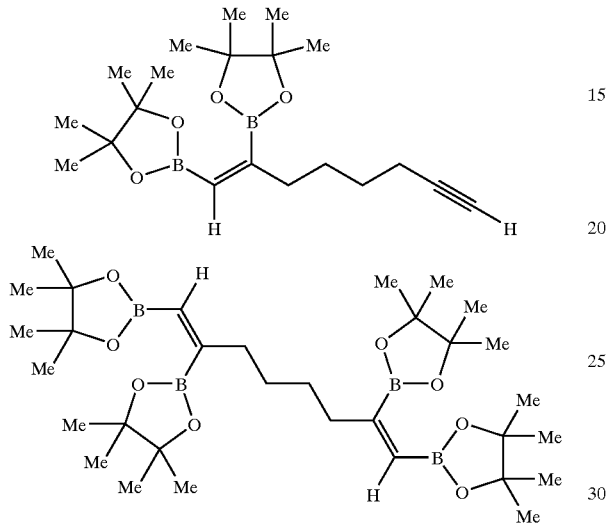

The pinacol ester of diboronic acid (0.254 g; 1.0 mmole), 1,7-octadiyne (0.152 g; 1.4 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 14 hours. GC analysis showed a peak at 13.2 minutes (71%) corresponding to the diboronic ester of 1,7-octadiyne, and a peak at 20.3 minutes (24%) corresponding to the tetraboronic ester of 1,7-octadiyne.

Example 46

4,4,5,5-Tetramethyl-2-[(E)-2-(4,4,5,5-tetramethyl-1,3,2-dioxaborolan-2-yl)-1-octen-7-ynyl]-1,3,2-dioxaborolane 4,4,5,5-Tetramethyl-2-[(1E,7E)-2,7,8-tris(4,4,5,5-tetramethyl-1,3,2-dioxaborolan-2-yl)-1,7-octadienyl]-1,3,2-dioxaborolane The pinacol ester of diboronic acid (0.254 g; 1.0 mmole), 1,7-octadiyne (0.055 g; 0.52 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 14 hours. GC analysis showed a peak at 13.2 minutes (1%) corresponding to the diboronic ester of 1,7-octadiyne, and a peak at 20.3 minutes (87%) corresponding to the tetraboronic ester of 1,7-octadiyne.

Example 47

2-[(Z)-1-Butyl-2-(4,4,5,5-tetramethyl-1,3,2-dioxaborolan-2-yl)-1-octen-3-ynyl]-4,4,5,5-tetramethyl-1,3,2-dioxaborolane 2-[(1Z,3Z)-1-Butyl-2,3,4-tris(4,4,5,5-tetramethyl-1,3,2-dioxaborolan-2-yl)-1,3-octadienyl]-4,4,5,5-tetramethyl-1,3,2-dioxaborolane

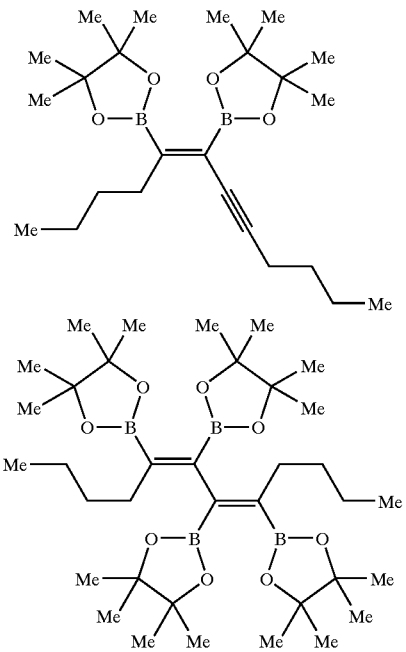

The pinacol ester of diboronic acid (0.254 g; 1.0 mmole), 5,7-dodecadiyne (0.250 g; 1.5 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 14 hours. GC analysis showed a peak corresponding to unreacted starting material (25%), a peak at 15.5 minutes (72%) corresponding to the diboronic ester of 5,7-dodecadiyne, and a peak at 17.4 minutes (2%) corresponding to the tetraboronic ester of 5,7-dodecadiyne.

Example 48

2-[(Z)-1-Butyl-2-(4,4,5,5-tetramethyl-1,3,2-dioxaborolan-2-yl)-1-octen-3-ynyl]-4,4,5,5-tetramethyl-1,3,2-dioxaborolane And 2-[(1Z,3Z)-1-Butyl-2,3,4-tris(4,4,5,5-tetramethyl-1,3,2-dioxaborolan-2-yl)-1,3-octadienyl]-4,4,5,5-tetramethyl-1,3,2-dioxaborolane The pinacol ester of diboronic acid (0.254 g; 1.0 mmole), 5,7-dodecadiyne (0.080 g; 0.49 mmoles) and tetrakis(triphenylphosphine)platinum (0.037 g; 0.030 mmoles) were placed in a Schlenk tube under an atmosphere of nitrogen. DMF (5 mL, dried over 4 Å molecular sieve) was added under argon, and the tube was heated at 80° C. with stirring for 14 hours. GC analysis showed a peak at 15.5 minutes (4%) corresponding to the diboronic ester of 5,7-dodecadiyne, and a peak at 17.4 minutes (95%) corresponding to the tetraboronic ester of 5,7-dodecadiyne.

Example 49

4,4,5,5-Tetramethyl-2-[(E)-3-phenyl-2-propenyl]-1,3,2-dioxaborolane

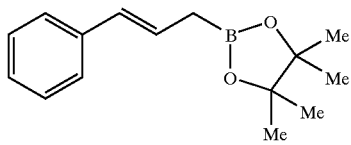

The pinacol ester of diboronic acid (0.254 g; 1.0 mmole), trans-cinnamyl acetate (0.176 g; 1.0 mmoles) and tris(dibenzylideneacetone)dipalladium (0.027 g; 0.030 mmoles) were placed in a Schlenk tube under an atmosphere of nitrogen. Methanol (5 mL, dried over 4 Å molecular sieve) was added under argon, and the tube was heated at 50° C. with stirring for 63 hours. GC analysis showed a peak corresponding to the boronic ester product at 10.2 minutes (60% conversion), as the sole product.

Example 50

2-[(Z)-2-(4H-1,3,2-Benzodioxaborinin-2-yl)-1,2-diphenylethenyl]-4H-1,3,2-benzodioxaborinine

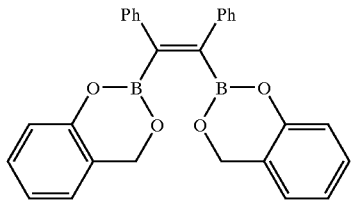

The 2-hydroxybenzyl alcohol ester of diboronic acid (0.266 g; 1.0 mmole), diphenylacetylene (0.176 g; 0.99 mmole) and tetrakis(triphenylphosphine)platinum (0.037 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 51

2-[(Z)-1,2-Diphenyl-2-(4,4,6-trimethyl-1,3,2-dioxaborinan-2-yl)ethenyl]-4,4,6-trimethyl-1,3,2-dioxaborinane

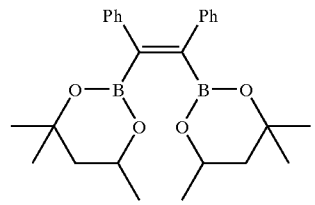

The 2-methyl-2,4-pentanediol ester of diboronic acid (0.256 g; 1.0 mmole), diphenylacetylene (0.177 g; 1.0 mmole) and tetrakis(triphenylphosphine)platinum (0.038 g; 0.031 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 52

2-[(Z)-2-(5,5-Diethyl-1,3,2-dioxaborinan-2-yl)-1,2-diphenylethenyl]-5,5-diethyl-1,3,2-dioxaborinane

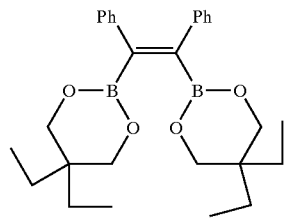

The 2,2-diethyl-1,3-propanediol ester of diboronic acid (0.283 g; 1.0 mmole), diphenylacetylene (0.179 g; 1.0 mmole) and tetrakis(triphenylphosphine)platinum (0.037 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 53

(2-{(Z)-2-[4-(Phenoxymethyl)-1,3,2-dioxaborolan-2-yl]-1,2-diphenylethenyl}-1,3,2-dioxaborolan-4-yl) methyl Phenyl Ether Or 4-(Phenoxymethyl)-2-{(Z)-2-[4-(phenoxymethyl)-1,3,2-dioxaborolan-2-yl]-1,2-diphenylethenyl}-1,3,2-dioxaborolane

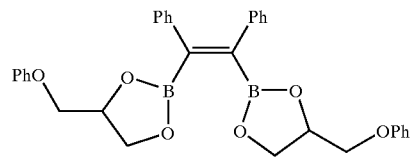

The 3-phenoxy-1,2-propanediol ester of diboronic acid (0.356 g; 1.0 mmole), diphenylacetylene (0.180 g; 1.0 mmole) and tetrakis(triphenylphosphine)platinum (0.037 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 54

(1S,2S,6R,8S)4-{(Z)-1,2-diphenyl-2-[(1R,2R,6S,8S)-2,9,9-trimethyl-3,5-dioxa-4-boratricyclo[6.1.1.02,6]dec-4-yl]ethenyl}-2,9,9-trimethyl-3,5-dioxa-4-boratricyclo[6.1.1.02,6]decane

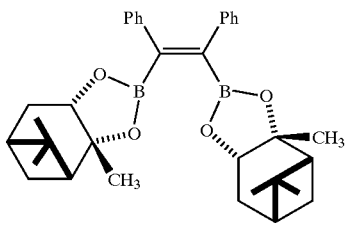

The 1R,2R,3S,5R-(−)-pinanediol ester of diboronic acid (0.359 g; 1.0 mmole), diphenylacetylene (0.179 g; 1.0 mmole) and tetrakis(triphenylphosphine)platinum (0.037 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 55

(3aR,6aS)-2-{(Z)-2-[(3aR,6aS)Tetrahydro-3aH-cyclopenta[d][1,3,2]dioxaborol-2-yl]-1,2-diphenylethenyl}tetrahydro-3aH-cyclopenta[d][1,3,2]dioxaborole

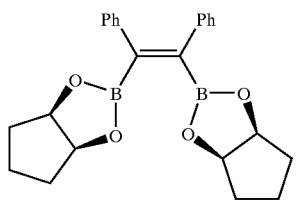

The cis-1,2-cyclopentanediol ester of diboronic acid (0.229 g; 1.0 mmole), diphenylacetylene (0.181 g; 1.0 mmole) and tetrakis(triphenylphosphine)platinum (0.039 g; 0.031 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 56

(3aR,6aS)-2-{(Z)-2-[(3aR,6aS)Tetrahydrofuro[3,4-d][1,3,2]dioxaborol-2-yl]-1,2-diphenylethenyl}tetrahydrofuro[3,4-d][1,3,2]dioxaborole

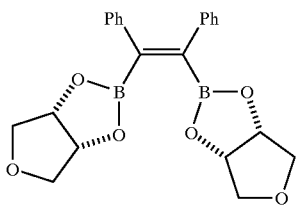

The 1,4-anhydroerythritol ester of diboronic acid (0.230 g; 1.0 mmole), diphenylacetylene (0.177 g; 1.0 mmole) and tetrakis(triphenylphosphine)platinum (0.037 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 57

2-[(Z)-1,2-Diphenyl-2-(4-phenyl-1,3,2-dioxaborolan-2-yl)ethenyl]-4-phenyl-1,3,2-dioxaborolane

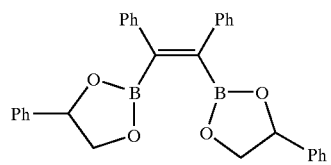

The 1-phenyl-1,2-ethanediol ester of diboronic acid (0.294 g; 1.0 mmole), diphenylacetylene (0.180 g; 1.0 mmole) and tetrakis(triphenylphosphine)platinum (0.038 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 58

(3aR,7aS)-2-{(Z)-2-[(3aR,7aS)Hexahydro-1,3,2-benzodioxaborol-2-yl]-1,2-diphenylethenyl}hexahydro-1,3,2-benzodioxaborole

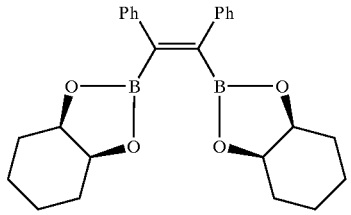

The cis-1,2-cyclohexanediol ester of diboronic acid (0.251 g; 1.0 mmole), diphenylacetylene (0.176 g; 0.99 mmole) and tetrakis(triphenylphosphine)platinum (0.038 g; 0.030 mmole) were placed in a Schlenk tube open to the atmosphere. Toluene (5 mL, dried over 4 Å molecular sieve) was added, and the sealed tube was heated at 80° C. with stirring for 72 hours. GC analysis showed the corresponding diboronic ester of diphenylacetylene to have formed.

Example 59

4-[(E)-1,2-Diphenyl-2-(4,4,5,5-tetramethyl-1,3,2-dioxaborolan-2-yl)ethenyl]phenol One pot synthesis of

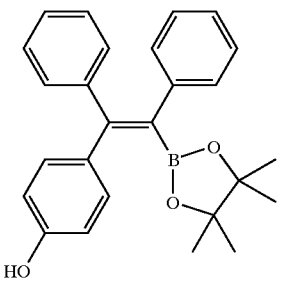

The 1,2-bis(boronic acid pinacol ester)-1,2-diphenylethene was obtained following the method described in Example 6. After addition of PdCl2(dppf).CH2Cl2 (27 mg), excess p-iodophenol (0.35 g) and K2CO3 (0.45 g) the solution was heated for a further 21.5 h at 80° C. GC analysis of the solution showed only one major peak (at 19.2 mins retention time) and was shown by GC/MS to be due to the tri-aryl product.

The diboron addition to the acetylene can be carried out with the same palladium catalyst as was used for the coupling reaction (see Example 4). Then both reactions are catalysed by the same catalyst.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A process for preparing an organoboron compound having one or more organoboron residues which comprises:
   (i) reacting an olefinic compound having at least one carbon to carbon double bond or an acetylenic compound having at least one carbon to carbon triple bond with a diboron derivative in the presence of a Group 8–11 metal catalyst to form an organoboron compound having an organoboronate residue on at least one carbon atom of the respective double or triple bond;
   wherein said olefinic or acetylenic compound has at least one active hydrogen containing substituent selected from the group consisting of hydroxy, amino, imino, carboxy, carboxylato, carboximidyl, sulfo, sulfinyl, sulfinimidyl, sulfinohydroximyl, sulfonimidyl, sulfondiimidyl, sulfonohydroximyl, sulfamyl, phosphinyl, phosphinimidyl, phosphonyl, dihydroxyphosphanyl, hydroxyphosphanyl, phosphono, phosphonato, hydrohydroxyphosphoryl, allophanyl, guanidino, hydantoyl, ureido, and ureylene, and wherein said reaction of the olefinic or acetylenic compound with the diboron derivative is an addition reaction across the double or triple bond respectively, or in the case of two or more conjugated carbon to carbon double bonds, the reaction introduces organoboronate residues on distal carbon atoms participating in the conjugation, resulting in loss of conjugation, or, in the case of an α,β-unsaturated carbonyl compound, the reaction introduces a single organoboronate residue on the β-carbon, resulting in loss of α,β-unsaturation, and
   (ii) optionally heating the reaction mixture to result in some hydrodeboronation.

2. A process for covalently coupling organic compounds which comprises:
   (i) reacting an olefinic compound having at least one carbon to carbon double bond or an acetylenic compound having at least one carbon to carbon triple bond with a diboron derivative in the presence of a Group 8–11 metal catalyst to form an organoboron intermediate having an organoboronate residue on at least one carbon atom of the respective double or triple bond;
   wherein said reaction of the olefinic or acetylenic compound with the diboron derivative is an addition reaction across the double or triple bond respectively, or, in the case of two or more conjugated carbon to carbon double bonds, the reaction introduces organoboronate residues on distal carbon atoms participating in the conjugation, resulting in loss of conjugation, or, in the case of an α,β-unsaturated carbonyl compound, the reaction introduces a single organoboronate residue on the β-carbon, resulting in loss of α,β-unsaturation,
   (ii) adding water, water and a suitable base, or a mild oxidising agent, to decompose excess diboron derivative, and
   (iii) reacting the organoboron intermediate with an organic compound having a halogen or halogen-like substituent at a coupling position in the presence of a Group 8–11 metal catalyst and a suitable base, whereby the olefinic or acetylenic compound is coupled to the organic compound via a direct bond between the carbon atom having the organoboronate residue and the coupling position.

3. A process according to claim 2 conducted in a single pot.

4. A process according to claim 2 wherein the base added to decompose the diboron derivative is employed to catalyse the coupling reaction.

5. A process according to claim 1 wherein the olefinic or acetylenic compound is selected from the group consisting of optionally substituted straight chain, branched or cyclic alkenes, and molecules, monomers and macromolecules which include at least one carbon to carbon double bond; α,β-unsaturated carbon compounds; optionally substituted straight chain, branched or cyclic alkynes and molecules, monomers and macromolecules which include at least one carbon to carbon triple bond.

6. A process according to claim 5 wherein the olefinic compound is a conjugated diene, an organic compound having a leaving group in an allylic position, or an organic compound having adjacent double bonds.

7. A process according to claim 2 wherein the olefinic compound is different from the organic compound.

8. A process according to claim 2 wherein the organoboron intermediate is isolated prior to reaction with the organic compound.

9. A process according to claim 2 wherein the organic compound is an aromatic or pseudoaromatic ring compound having a halogen or halogen-like substituent at a coupling position.

10. A process according to claim 2 wherein the organic compound is an olefinic compound having a halogen or halogen-like substituent at a vinylic coupling position.

11. A process according to claim 2 wherein the organic compound is an aliphatic compound having a halogen or halogen-like substituent at a coupling position.

12. A process according to claim 2 wherein the organic compound is an acetylenic compound having a halogen or halogen-like substituent at a coupling position.

13. A process according to claim 2 wherein the olefinic or acetylenic compound has an active hydrogen containing substituent.

14. A process according to claim 6 wherein the olefinic compound has a leaving group at an allylic substitution position which is replaced with an organoboronate residue following reaction with the diboron derivative.

15. A process according to claim 1 wherein the organoboron compound is hydrolyzed to produce an organic boronic acid.

16. A process according to claim 1 wherein the reaction with the diboron derivative is conducted in the presence of a promoter.

17. A process according to claim 16 wherein the promoter is air or oxygen.

18. A process according to claim 2 wherein the organic compound has more than one halogen or halogen-like substituent.

19. A process according to claim 1 wherein the Group 8–11 metal catalyst comprises palladium, nickel or platinum.

20. A process according to claim 19 wherein the Group 8–11 metal catalyst is a platinum catalyst.

21. A process according to claim 20 wherein the platinum catalyst is a platinum complex.

22. A process according to claim 21 wherein the platinum complex is selected from the group consisting of $Pt_3(dba)_2$, $Pt(PPh_3)_2Cl_2$, $PtCl_2$, $Pt(OAc)_2$, $PtCl_2(dppf)CH_2Cl_2$, $Pt(PPh_3)_4$ and related catalysts which are complexes of phosphine ligands, phosphite ligands, or other suitable ligands containing P and/or N atoms for co-ordinating to the platinum atoms.

23. A process according to claim 21 wherein the platinum complex is tethered on a solid support.

24. A process according to claim 20 wherein the platinum catalyst is selected from platinum black, platinum on carbon and platinum clusters or a platinum complex or a platinum complex tethered on a solid support.

25. A process according to claim 19 wherein the Group 8–11 metal catalyst is a palladium catalyst.

26. A process according to claim 23 wherein the catalyst is selected from the group consisting of palladium black, palladium on carbon, palladium clusters and palladium in porous glass.

27. A process according to claim 19 wherein the catalyst is a nickel complex.

28. A process according to claim 27 wherein the catalyst is selected from the group consisting of nickel black, Raney nickel, nickel on carbon and nickel clusters or a nickel complex or a nickel complex tethered on a solid support.

29. A process according to claim 1 wherein the diboron derivative is an ester or other stable derivative of diboronic acid.

30. A process of claim 1 conducted in the presence of a protic solvent.

31. A process of claim 2 wherein the suitable base is selected from the group consisting of aryl and alkyl carboxylates, carbonates, fluorides and phosphates of Li, Na, K, Rb, Cs, ammonium and alkylammonium.

32. A process of claim 2 wherein the suitable base is selected from the group consisting of aryl and alkyl carboxylates, fluorides, hydroxides and carbonates of Li, Na, K, Rb, Cs, ammonium, alkylammonium, Mg, Ca and Ba; phosphates, and arylphosphates of Li, Na, K, Rb and Cs; phosphate esters of Li, Na, K, Rb and Cs, phenoxides of Li, Na, K, Rb and Cs; alkoxides of Li, Na, K, Rb and Cs; and thallium hydroxide.

33. A process of claim 2 wherein the suitable base is selected from cesium carbonate, potassium carbonate, potassium phosphate and alkali metal hydroxides.

34. A process of claim 2 wherein one of said olefinic compound and said organic compound is a polymer.

35. A process of claim 2 wherein either the olefinic compound or the organic compound is chemically linked to a solid polymer support.

36. A process according to claim 1 wherein the formed organoboron compound has an organoboronate residue on each carbon atom of the respective double or triple bond.

37. A process according to claim 36 wherein the reaction mixture is heated in the presence of a base such that some or all of the organic intermediate undergoes monohydroboronation.

38. A process according to claim 2 wherein the diboron derivative is chiral having an enantiomeric excess of one form relative to another such that the formed organoboron intermediate is chiral having an enantiomeric excess.

39. A process according to claim 1 wherein the diboron derivative is chiral having an enantiomeric excess of one form relative to another such that the formed organoboron compound is chiral having an enantiomeric excess of one form relative to another.

40. Organoboron compounds selected from the group consisting of:

2-[(Z)-2-(5,5-dimethyl-1,3,2-dioxaborinan-2-yl)-1,2-diphenylethenyl]-5,5-dimethyl-1,3,2-dioxaborinane, 2-[(Z)-2-(5,5-dimethyl-1,3,2-dioxaborinan-2-yl)-1-ethyl-1-butenyl]-5,5-dimethyl-1,3,2-dioxaborinane, 2-[(Z)-2-(5,5-dimethyl-1,3,2-dioxaborinan-2-yl)-1-phenyl-1-butenyl]-5,5-dimethyl-1,3,2-dioxaborinane, methyl (Z)-2,3-bis(4,4,5,5-tetramethyl-1,3,2-dioxaborolan-2-yl)-2-nonenoate, (E)4-phenyl-3-(4,4,5,5-tetramethyl-1,3,2-dioxaborolan-2-yl)-3-buten-2-one, (Z)-4-phenyl-4-(4,4,5,5-tetramethyl-1,3,2-dioxaborolan-2-yl)-3-buten-2-one, 2-[(E)-1-(1-cyclohexen-1-yl)-2-(4,4,5,5-tetramethyl-1,3,2-dioxaborolan-2-yl)ethenyl]-4,4,5,5-tetramethyl-1,3,2-dioxaborolane, 1-[(E)-1,2-bis(4,4,5,5-tetramethyl-1,3,2-dioxaborolan-2-yl)ethenyl]cyclohexanol, (E)-N,N-dimethyl-2,3-bis(4,4,5,5-tetramethyl-1,3,2-dioxaborolan-2-yl)-2-propen-1-amine, (E)-3-ethyl-1,2-bis(4,4,5,5-tetramethyl-1,3,2-dioxaborolan-2-yl)-1-penten-3-amine, (E)-N,N-di(2-propynyl)-2,3-bis(4,4,5,5-tetramethyl-1,3,2-dioxaborolan-2-yl)-2-propen-1-amine, 4,4-dimethyl-3-(4,4,5,5-tetramethyl-1,3,2-dioxaborolan-2-yl)cyclohexanone, 4,4,5,5-tetramethyl-2-[4-(4,4,5,5-tetramethyl-1,3,2-dioxaborolan-2-yl)-2-cyclohexen-1yl]-1,3,2-dioxaborolane, (Z)-1,5-diphenyl-5-(4,4,5,5-tetramethyl-1,3,2-dioxaborolan-2-yl)-1-penten-3-one, 3-phenyl-3-(4,4,5,5-tetramethyl-1,3,2-dioxaborolan-2-yl) propanal, 4,4,5,5-tetramethyl-2-[8-(4,4,5,5-tetramethyl-1,3,2-dioxaborolan-2-yl)-2,4,6-cyclooctatrien-1-yl]-1,3,2-dioxaborolane, 4,4,5,5-tetramethyl-2-[6-(4,4,5,5-tetramethyl-1,3,2-dioxaborolan-2-yl)-2,4,7-cyclooctatrien-1-yl]-1,3,2-dioxaborolane, 4,4,5,5-tetramethyl-2-[8-(4,4,5,5-tetramethyl-1,3,2-dioxaborolan-2-yl)-4-cycloocten-1-yl]-1,3,2-dioxaborolane, 4,4,5,5-tetramethyl-2-[9-(4,4,5,5-tetramethyl-1,3,2-dioxaborolan-2-yl)tricyclo[5.2.1.02,6]dec-3-en-8-yl]-1,3,2-dioxaborolane, 4,4,5,5-tetramethyl-2-[3-(4,4,5,5-tetramethyl-1,3,2-dioxaborolan-2-yl)tricyclo[5.2.1.02,6]dec-8-en-4-yl]-1,3,2-dioxaborolane, 4,4,5,5-tetramethyl-2-(4-methylcyclohexyl)-1,3,2-dioxaborolane, 4,4,5,5-tetramethyl-2-(3-methylcyclohexyl)-1,3,2-dioxaborolane, 4,4,5,5-tetramethyl-2-[(E)-2-(4,4,5,5-tetramethyl-1,3,2-dioxaborolan-2-yl)-1-octen-7-ynyl]-1,3,2-dioxaborolane, 4,4,5,5-tetramethyl-2-[(1E,7E)-2,7,8-tris(4,4,5,5-tetramethyl-1,3,2-dioxaborolan-2-yl)-1,7-octadienyl]-1,3,2-dioxaborolane, 2-[(Z)-1-butyl-2-(4,4,5,5-tetramethyl-1,3,2-dioxaborolan-2-yl)-1-octen-3-ynyl]4,4,5,5-tetramethyl-1,3,2-dioxaborolane, 2-[(1Z,3Z)-1-butyl-2,3,4-tris(4,4,5,5-tetramethyl-1,3,2-dioxaborolan-2-yl)-1,3-octadienyl]-4,4,5,5-tetramethyl-1,3,2-dioxaborolane, 2-[(Z)-2-(4H-1,3,2-benzodioxaborinin-2-yl)-1,2-diphenylethenyl]-4H-1,3,2-benzodioxaborinine, 2-[(Z)-1,2-diphenyl-2-(4,4,6-trimethyl-1,3,2-dioxaborinan-2-yl)ethenyl]-4,4,6-trimethyl-1,3,2-dioxaborinane, 2-[(Z)-2-(5,5-diethyl-1,3,2-dioxaborinan-2-yl)-1,2-diphenylethenyl]-5,5-diethyl-1,3,2-dioxaborinane, (2-{(Z)-2-[4-(phenoxymethyl)-1,3,2-dioxaborolan-2-yl]-1,2-diphenylethenyl}-1,3,2-dioxaborolan-4-yl)methyl phenyl ether, (1S,2S,6R,8S)-4-{(Z)-1,2-diphenyl-2-[(1R,2R,6S,8S)-2,9,9-trimethyl-3,5-dioxa-4-boratricyclo[6.1.1.0²,⁶]dec-4-yl]ethenyl}-2,9,9-trimethyl-3,5-dioxa4-boratricyclo[6.1.1.0²,⁶]decane, (3aR,6aS)-2-{(Z)-2-[(3aR,6aS)tetrahydro-3aH-cyclopenta[d][1,3,2]dioxaborol-2-yl]-1,2-diphenylethenyl}tetrahydro-3aH-cyclopenta[d][1,3,2]dioxaborole, (3aR,6aS)-2-{(Z)-2-[(3aR,6aS)tetrahydrofuro[3,4-d][1,3,2]dioxaborol-2-yl]-1,2-diphenylethenyl}tetrahydrofuro[3,4-d][1,3,2]dioxaborole, 2-[(Z)-1,2-diphenyl-2-(4-phenyl-1,3,2-dioxaborolan-2-yl)ethenyl]-4-phenyl-1,3,2-dioxaborolane, and (3aR,7aS)-2-{(Z)-2-[(3aR,7aS)hexahydro-1,3,2-bexzodioxaborol-2-yl]-1,2-diphenylethenyl}hexahydro-1,3,2-benzodioxaborole.

41. A process according to claim 38 wherein the chirality of organoboron intermediate results in a coupled product having a chirality and an enantiomeric excess of one enantiomer relative to another.

* * * * *